(12) United States Patent
Valdes et al.

(10) Patent No.: US 11,081,225 B2
(45) Date of Patent: Aug. 3, 2021

(54) SYSTEM AND METHOD FOR VIRTUAL RADIATION THERAPY QUALITY ASSURANCE

(71) Applicant: The Trustees of the University of Pennsylvania, Philadelphia, PA (US)

(72) Inventors: Gilmer Valdes, Philadelphia, PA (US); Timothy Solberg, Philadelphia, PA (US); Ryan Scheuermann, Philadelphia, PA (US); Marc Bellerive, Philadelphia, PA (US); C. Y. Hung, Philadelphia, PA (US); Arthur Olszanski, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 558 days.

(21) Appl. No.: 15/563,411

(22) PCT Filed: Mar. 30, 2016

(86) PCT No.: PCT/US2016/024931
§ 371 (c)(1),
(2) Date: Sep. 29, 2017

(87) PCT Pub. No.: WO2016/160932
PCT Pub. Date: Oct. 6, 2016

(65) Prior Publication Data
US 2018/0085168 A1 Mar. 29, 2018

Related U.S. Application Data

(60) Provisional application No. 62/139,864, filed on Mar. 30, 2015.

(51) Int. Cl.
*G06F 17/10* (2006.01)
*G16H 20/40* (2018.01)
(Continued)

(52) U.S. Cl.
CPC ............ *G16H 20/40* (2018.01); *A61B 34/10* (2016.02); *G06F 19/00* (2013.01); *G06Q 10/04* (2013.01);
(Continued)

(58) Field of Classification Search
CPC ........ G06F 19/00; G16H 50/20; G06Q 10/04; G06Q 10/06395; G06Q 50/22
(Continued)

(56) References Cited

U.S. PATENT DOCUMENTS 8,927,921 B1 1/2015 Nelms et al.
10,513,737 B2 * 12/2019 Davicioni ............ C12Q 1/6886
(Continued)

FOREIGN PATENT DOCUMENTS

WO 2014/205128 12/2014

OTHER PUBLICATIONS

International Patent Application No. PCT/US2016/024931, Notification of Transmittal of the International Search Report and the Written Opinion of the International Searching Authority dated Jul. 1, 2016, 10 pages.

*Primary Examiner* — Andre Pierre Louis
(74) *Attorney, Agent, or Firm* — Morgan, Lewis & Bockius LLP

(57) ABSTRACT

A method comprises receiving one or more plan parameters of a first radiation treatment plan for a first patient and one or more passing rate data for the first treatment plan; generating a predictive model for passing rate data from the plan parameters of the first radiation treatment plan and the passing rate data for the first treatment plan; receiving one
(Continued)

or more plan parameters of a second radiation treatment plan for a second patient; and applying the predictive model to the plan parameters of the second radiation treatment to generate one or more predicted passing rate data for the plan parameters for the second patient.

17 Claims, 19 Drawing Sheets

(51) Int. Cl.
*G06Q 10/04* (2012.01)
*G06Q 10/06* (2012.01)
*G16H 70/20* (2018.01)
*A61B 34/10* (2016.01)
*G16H 50/20* (2018.01)
*G06F 19/00* (2018.01)
*A61N 5/10* (2006.01)

(52) U.S. Cl.
CPC ....... *G06Q 10/06395* (2013.01); *G16H 50/20* (2018.01); *G16H 70/20* (2018.01); *A61N 5/1028* (2013.01)

(58) Field of Classification Search
USPC .......................................................... 703/2
See application file for complete search history.

(56) References Cited

U.S. PATENT DOCUMENTS

| | | | |
|---|---|---|---|
| 2008/0301077 A1* | 12/2008 | Fung | G16H 50/20 706/46 |
| 2013/0337449 A1 | 12/2013 | Paik et al. | |
| 2014/0107390 A1 | 4/2014 | Brown et al. | |
| 2015/0005176 A1* | 1/2015 | Kim | C12Q 1/6872 506/2 |
| 2018/0291459 A1* | 10/2018 | Al-Deen Ashab | G01N 33/57434 |

* cited by examiner

| Group | Features |
|---|---|
| Clinacs 1,3,4 | 1. Weighted Average Irregularity Factor |
| | 2. Weighted Out of circle fractional area 40 |
| | 3. MU factor |
| | 4. SAS 5mm |
| | 5. Leaf Gap Moment 4 |
| Clinacs 2 | 1. Modulation factor |
| | 2. SAS 5mm |
| | 3. SAS 5mm |
| | 4. Out of circle fractional area 30 |
| | 5. SAS 10mm |
| TrueBeam | Average Perimeter |
| | Infield Area 1 |
| | Infield Area 4 |
| | Out of circle fractional Area 25 |
| | Infield Area 5 |

FIG. 14

| Database | Predicted | Re-measured |
|---|---|---|
| 93.6 | 97.2 | 98.2 |
| 96.60 | 93.5 | 95.5 |
| 91.8 | 95.8 | 93.4 |
| 92.4 | 96.1 | 94.6 |
| 90 | 93.6 | 95.2 |

FIG. 17

SYSTEM AND METHOD FOR VIRTUAL RADIATION THERAPY QUALITY ASSURANCE

CROSS REFERENCE TO RELATED APPLICATIONS

This Patent Application is a U.S. National Stage filing of International Patent Application No. PCT/US2016/024931, filed Mar. 30, 2016, which claims the benefit of priority of U.S. Provisional Patent Application No. 62/139,864, filed Mar. 30, 2015, the entire contents of which is incorporated herein by reference.

FIELD OF THE INVENTION

The present invention, according to some embodiments, relates to a method and system for quality assurance of radiation therapy, and in particular for Intensity Modulated Radiation Therapy (IMRT) applications.

BACKGROUND OF THE INVENTION

The course of radiation treatment of cancer patients could be divided in three major phases: 1) diagnostic and prescription; 2) simulation and Quality Assurance (QA); and 3) delivery. In diagnostic and prescription the location of the tumor, as well as the prescription of the amount of radiation that the tumor should receive, is decided.

SUMMARY OF THE INVENTION

The present invention relates to methods and systems for use in developing and providing quality assurance for Intensity Modulated Radiation Therapy plans.

In some embodiments, the invention includes a method that may include receiving one or more plan parameters of a first radiation treatment plan for a first patient and one or more passing rate data for the first radiation treatment plan. In some embodiments, the methods of the invention may include generating a predictive model for passing rate data from plan parameters of the first radiation treatment plan and the passing rate data for the first radiation treatment plan. In some embodiments, the methods of the invention may include receiving one or more plan parameters of a second radiation treatment plan for a second patient. In some embodiments, the methods of the invention may include applying the predictive model to the plan parameters of the second radiation treatment plan to generate one or more predicted passing rate data for the plan parameters for the second patient.

In some embodiments, the methods of the invention may include extracting one or more features associated with failure modes from the one or more passing rate data for the first radiation treatment plan. In some embodiments, the plan parameters of a first radiation treatment plan may include, for example, organ volume data for the first patient. Moreover, the plan parameters of a second radiation treatment plan may include organ volume data for the second patient.

In some embodiments, the plan parameters of a first radiation treatment plan may include one or more of (1) radiation energies utilized in a treatment plan; (2) parameters characterizing collimator jaw positions used in a treatment plan; (3) parameters characterizing collimator angles used in a treatment plan; (4) parameters describing the distribution of MLC leaf pair openings used for delivery of a treatment plan; (5) parameters describing an area of MLC and jaw defined apertures in delivery control points for a treatment plan; (6) parameters relating monitor units utilized in a treatment plan to fractional plan dose; (7) parameters describing MLC aperture geometry in each delivery control point; (8) parameters describing a proportion of radiation delivered at different distances from a central axis; (9) parameters describing a proportion of radiation delivered with different MLC leaf geometries; (10) parameters describing MLC and jaw geometries; (11) parameters describing Linac limitations; (12) parameters describing limitations of a dose calculation algorithm; and (13) parameters describing a calculated dose pattern of a treatment plan projected on a phantom.

In some embodiments, the plan parameters of a first radiation treatment plan may be weighted by the proportion of total monitor units delivered in each control point to the total monitor units delivered in the radiation treatment plan. In some embodiments, organ volume data may include one or more parameters, such as, Gross Tumor Volume to critical organs, organ type, and dose constraints.

In some embodiments, the passing rate data for the first treatment plan may include dose difference data, distance to agreement data, gamma passing rate data, or a combination thereof. In some embodiments, the predictive model may include a generalized linear model. In some embodiments, the predictive model may be generated using a Lasso selection method.

In some embodiments of the invention, a failure mode may be defined as having greater than 3 percent dose difference and/or 3 mm distance to agreement. In some embodiments, a failure mode may be defined as having greater than 2 percent dose difference and/or 2 mm distance to agreement. In some embodiments, the methods of the invention may include modifying the second treatment plan if the generated pass rates include a failure mode. In some embodiments, the methods of the invention may include treating the patient in accordance with the second treatment plan if the generated pass rates do not include a failure mode.

In some embodiments, the invention may include a system for generating predictive pass rates for radiation therapy. In some embodiments, the system of the invention may include a data-processing system. In some embodiments, the system may include a plan database that includes one or more treatment plans for a first patient. In some embodiments, the system may include a passing rate database that includes one or more passing rates associated with each of the treatment plans in the plan database. In some embodiments, the system may include a predictive model for generating predictive pass rates based on the plan database and the passing rate database. In some embodiments, the data-processing system of the invention may receive or otherwise communicate with the plan database and passing rate database and implements the predictive model.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

FIG. 14 is a table describing the important features for each model described in Example 2. Features are different for each of the linac groups, which may suggest the need for separate models.

FIG. 17 is a table that provides an example of 5 plans whose measurements disagree on more than 3% with the predicted values and, after re-delivery, the values fell within the 3% error.

DETAILED DESCRIPTION

Figure 1:
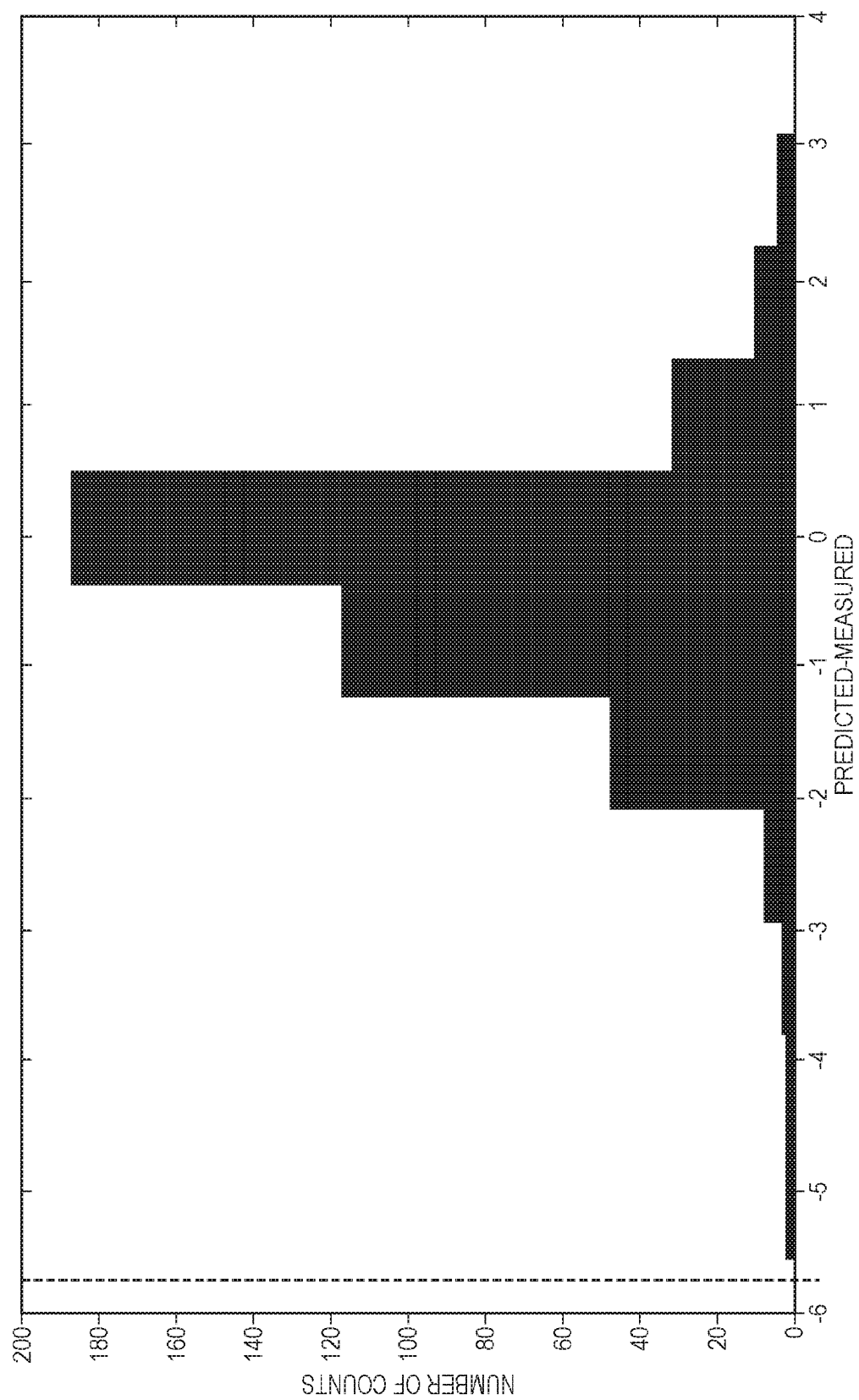
FIG. 1 is a bar graph showing the residual errors of predicted minus measured values of 3 p/3 mm DTA passing rates for 498 IMRT plans using a method in accordance with an embodiment of the invention.

During simulation and Quality Assurance (QA), a patient specific plan with all indications on how to deliver the amount of radiation prescribed to the tumor is developed. The plan is usually developed in software that uses 3D information of the anatomy of the patients as well as models of the Linear Accelerators (Linacs) that are going to be used to deliver the radiation. The most popular technique to deliver radiation to tumors is Intensity Modulated Radiation Therapy (IMRT). Due to possible disagreements between the software where the plan is developed and the actual delivery of radiation, each plan is measured on the Linacs using different types of detectors before the same is delivered to the patients. This step is called IMRT QA and is required before the delivery of radiation to the patient. Measurement based IMRT QA is time consuming and its relevance in catching clinically relevant errors has been questioned.

It is common practice to measure 2D and 3D dose distributions prior to treating any patient using IMRT. To assess the integrity of the delivery, the measured dose and dose distribution(s) are compared with those predicted by the planning system. A number of different metrics are commonly used to assess agreement of the two distributions, including point-by-point dose difference, distance-to-agreement (DTA), and the gamma index which combines both DTA and dose evaluation[1-4]. These metrics are very sensitive to the method used to analyze the data. Analysis can be performed per beam or per plan (composite), and can be performed by normalizing the plans or fields with respect to the global maximum dose or local dose, typically with the requirement that 90% of the points pass the particular criterion in order for a plan to be considered clinically acceptable[1]. When global analysis is performed, the IMRT QA process is generally insensitive and unable to catch significant clinical errors[5-9]. Use of log files and independent dose calculations may be used as substitutes for measurement based IMRT QA[5,7]. However, measurement based IMRT QA using a global normalization is the standard in most clinics, though a lack of consensus on how the analysis is performed (per field vs per plan, global vs local dose comparison, dose normalization point/value, threshold, interpolations) remains.

Even within a specific disease site, passing rates can show large variability, thus plan specific passing rates with respective confident intervals should be the ultimate goal. In order to use a plan specific threshold, a method and system that include an algorithm capable of predicting passing rates with clinically relevant accuracy is needed. Once the dependence of the passing rate on the complexity metric has been removed, any variation in the passing rate would be due to random noise. In pursuit of that goal, different complexity metrics may be used to characterize treatment plans, with the intention of correlating them with IMRT QA passing rates.

These metrics fall into two general categories: fluence map-based[12-15] or aperture-based[15-20]. Some of these metrics may be incorporated into treatment planning systems (TPS), with a goal of producing plans that are more likely to pass QA[21-23]. Nevertheless, different aspects of the complexity of the plans that might interact in any given case are associated with plans failing QA. As a result, only weak correlations have been found between passing rates and these metrics[12-20]. Therefore, a method and system that include an algorithm that integrates different complexity metrics and it is capable of predicting IMRT QA passing rates has yet to be developed. The present invention provides a method and system that include an algorithm that predicts passing rates a priori (Virtual IMRT QA) and was developed using Machine Learning to maximize the prediction accuracy of the algorithm in out of sample data.

In some embodiments that can be used alone or in combination with virtual Quality Assurance, as described further below, it is contemplated replacing IMRT QA with an analysis of the Log files of the Linacs after the delivery of each fraction of radiation can be conducted. In still other embodiments there can be included products that analyze the Log files of the Linacs as well as independent dose calculation algorithms to validate the treatment planning system.

However, the Log files approach to IMRT QA typically catches problems a posteriori and does not answer the fundamental question of whether a plan could be delivered according to the limitations of the Linacs with minimal or a clinically acceptable error. Similarly, independent dose calculations do not address the issue of deliverability either.

Thus, in one embodiment, a virtual approach to Quality Assurance, or Virtual QA, answers the question of whether the plan could be delivered with an acceptable error, a priori. In some embodiments, virtual QA, optionally used together with the Log files approach and/or independent dose calculations, allows more efficient and reliable substitution of the current measurement-based IMRT QA method.

The present subject matter will now be described more fully hereinafter with reference to the accompanying Figures, in which representative embodiments are shown. The present subject matter can, however, be embodied in different forms and should not be construed as limited to the embodiments set forth herein. Rather, these embodiments are provided to describe and enable one of skill in the art.

Figure 3:
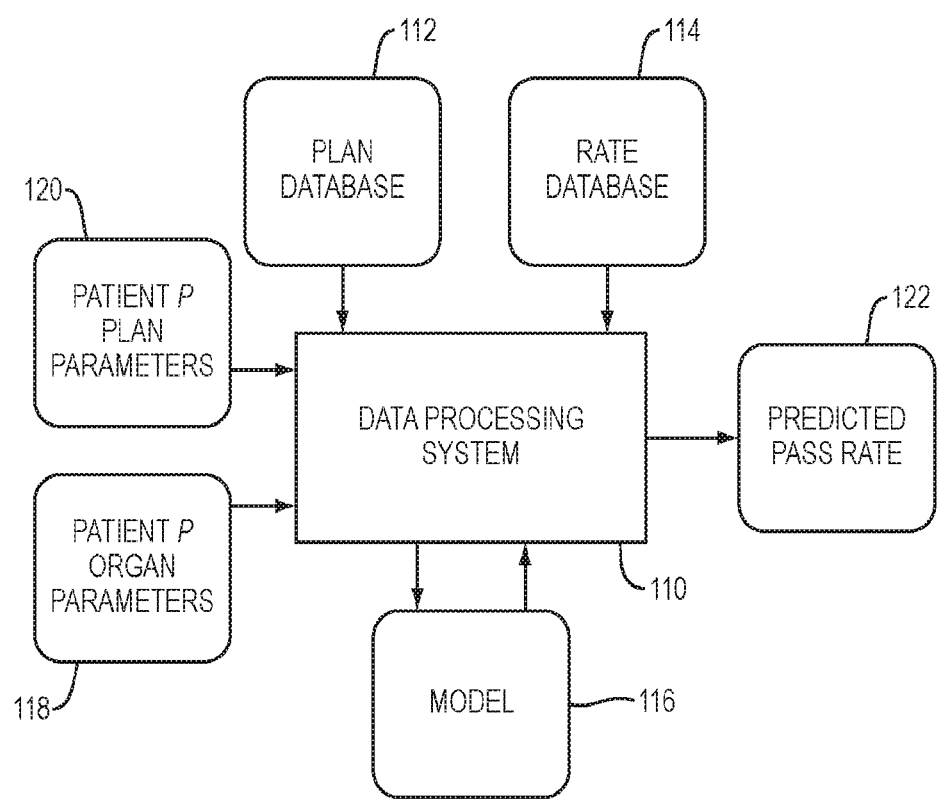
FIG. 3 depicts the salient elements of a virtual IMRT QA system 110, in accordance with an embodiment of the invention.

Referring to FIG. 3, a data-processing system 110 receives one or more plan parameters from a first radiation treatment plan (e.g. from a plan database 112) and one or more passing rates for each of the plan parameters (e.g. from a passing rate database 114). The data-processing system 110 extracts features associated with failure modes from the population passing rate database 114. Using the one or more plan parameters and passing rates and the extracted features associated with failure modes, the data-processing system 110 generates a machine learning model 116 for predicting passing rates. In some embodiments, a machine learning model may include an algorithm or series of computer-implemented rules or commands that are based on raw data. In some embodiments a machine learning model may be programmed to modify an algorithm or series of computer-implemented rules or commands as additional raw data is provided to the model (e.g. an algorithm may modify rules or commands to provide an improved fit as additional raw data is provided). Data processing system 110 further receives organ data for patient P 118 and one or more radiation treatment plan parameters for patient P 120. Data-processing system 110 generates one or more predicted pass rates 122 for the one or more radiation treatment plan parameters 120 for patient P from the machine learning model 116.

Figure 4:
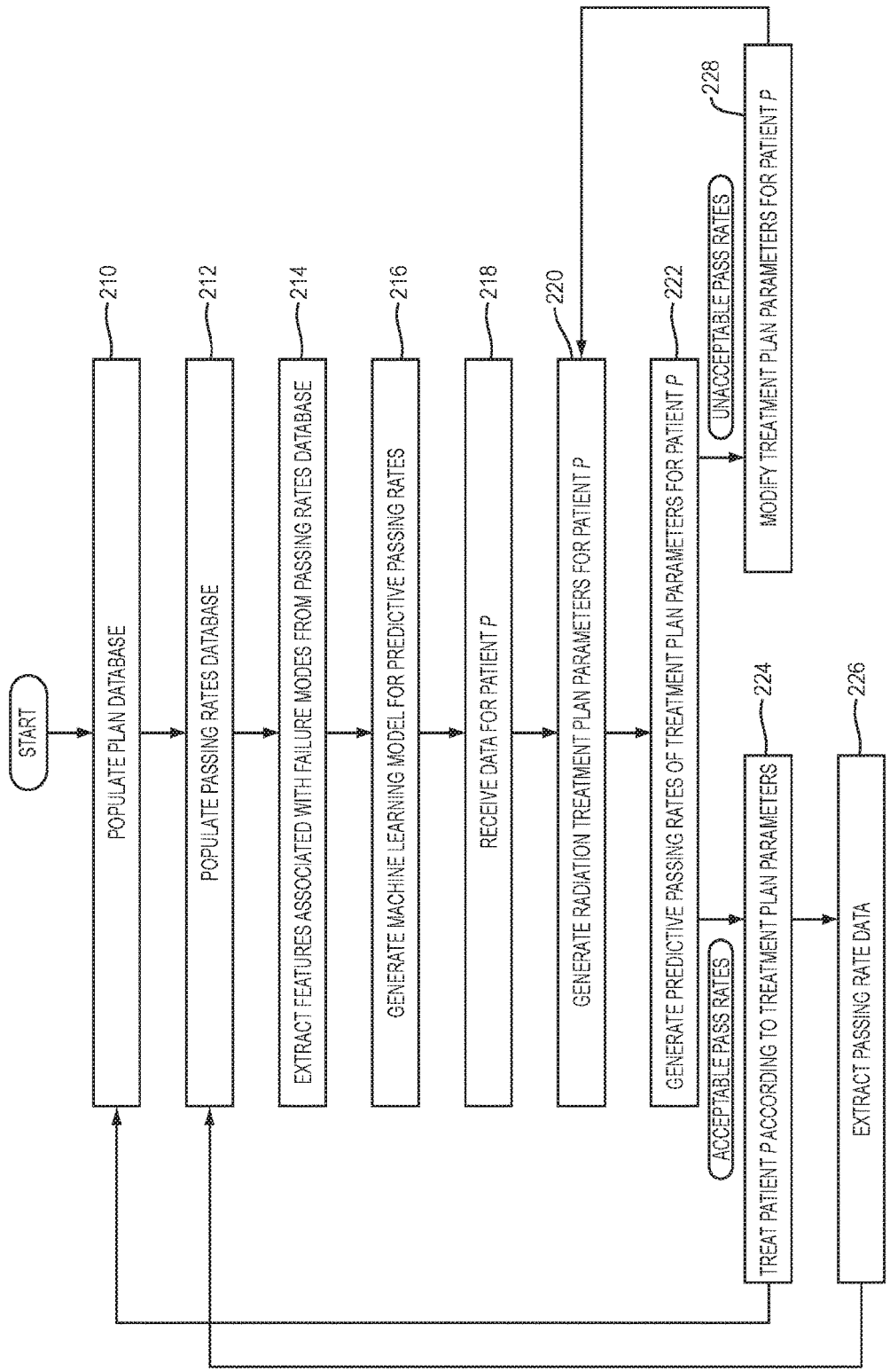
FIG. 4 depicts a flowchart of the salient tasks performed by the data processing system of FIG. 3, in accordance with an embodiment of the invention.

Referring to FIG. 4, in step 210 a plan database 112 is populated and in step 212 a passing rates database 114 with passing rates corresponding to the plans in plan database 112 is populated. In step 214, the data-processing system 110 extracts features associated with failure modes from the passing rates database 114. In step 216 the data-processing system uses the features associated with failure modes from the passing rates database 114, optionally together with data provided in the plan database 112 and/or the passing rate database 114 to generate a machine learning model 116 for predicting passing rates. In step 218 organ data for patient P 118 are provided and in step 220 plan parameters for a proposed treatment plan for patient P 120 are provided, then in step 222 model 116 is applied to the organ data 118 and plan parameters 120 to generate predictive passing rates 122 of treatment for the plan parameters for patient P. If the predictive passing rates 122 are acceptable, in step 224 patient P is treated according to the treatment plan parameters. In some embodiments in step 226 passing rate data can be extracted after patient treatment, e.g., using Log files from linacs. The treatment plan parameters used and the passing rate data extracted can be added to the plan database 112 and passing rates database 114 for future use. If the predictive passing rates 122 are unacceptable, the treatment plan for patient P is modified in step 228 and the machine learning model 116 is applied to the modified treatment plan for patient P to predict passing rates of the modified plan parameters. The process of iteratively modifying the treatment plan parameters and generating predictive pass rates may be repeated once, twice, or a plurality of times until a plan is provided for which the machine learning model 116 provides acceptable passing rates.

Figure 5:
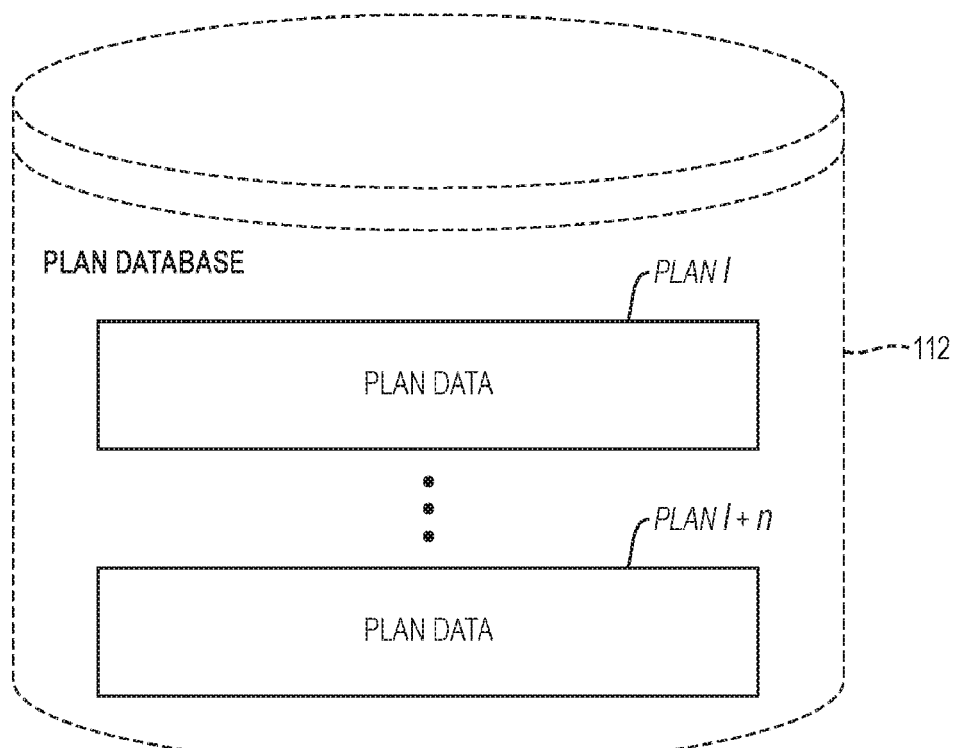
FIG. 5 depicts a block diagram of the salient data stored in plan database of FIG. 3, in accordance with an embodiment of the invention.
Figure 6:
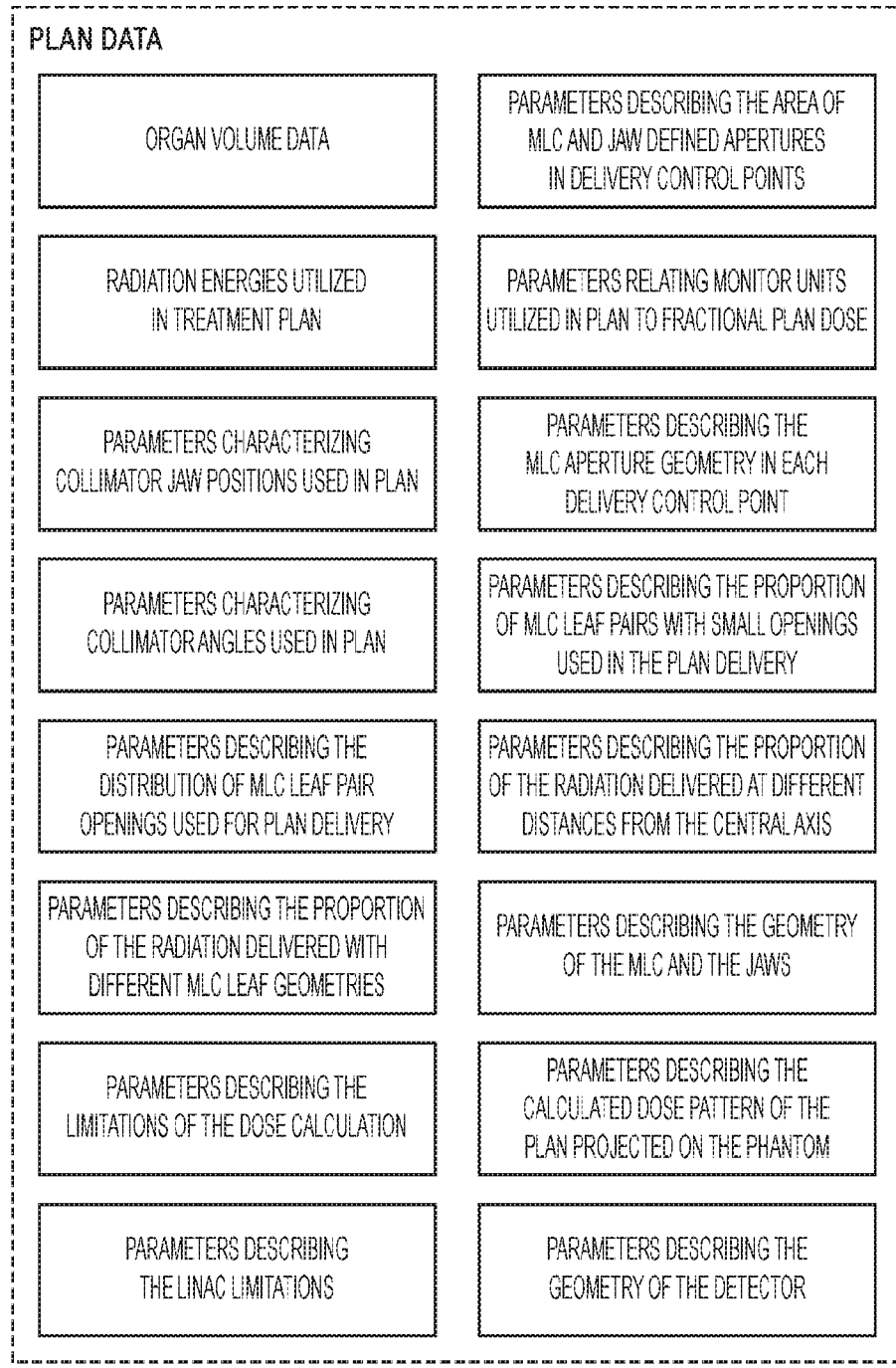
FIG. 6 depicts the contents of plan data, as shown in FIG. 5, in accordance with an embodiment of the invention.

Referring to FIGS. 5 and 6, plan database 112 may include one or more sets of plan data (e.g. Plan i through Plan i+n, where i represents a first plan, and n can be any integer). In some embodiments, plan data in plan database 112 may include any metrics useful to an expert practitioner for planning a radiation treatment. For example, plan data in the plan database may include a description of the desired dose distribution in terms of dose volume constraints for the delineated target tissue(s) as well as for the delineated surrounding organs at risk (OAR) and non-target tissues. In some embodiments a treatment plan may show the dose distribution and the beam parameters required for treatment of a particular patient. In the illustrative example, plan database 112 includes organ volume data, geometric characterization of target volume and organ at risk (OAR), 3D dose distribution, dose volume histogram (DVH), target volume, target dose and DVH prescriptions, OAR dose and sparing DVH prescriptions, physician sparing preferences and characteristics, machine-specific features, and additional patient-specific features. In some embodiments plan database 112 may include any or all of: radiation energies utilized in treatment plan; parameters characterizing collimator jaw positions used in plan; parameters characterizing collimator angles used in plan; parameters describing the distribution of multi-leaf collimator (MLC) leaf pair openings used for plan delivery; parameters describing the area of MLC and jaw defined apertures in delivery control points; parameters relating monitor units utilized in plan to fractional plan dose; parameters describing the MLC aperture geometry in each delivery control point; parameters describing the proportion of MLC leaf pairs with small openings used in the plan delivery; parameters describing the proportion of the radiation delivered at different distances from the central axis; parameters describing the proportion of the radiation delivered with different MLC leaf geometries; parameters describing the geometry of the MLC and the jaws; parameters describing the Linac Limitations; parameters describing the limitations of the dose calculation algorithm; parameters describing the calculated dose pattern of the plan projected on the phantom; and parameters describing the geometry of the detector. In some embodiments plan parameters are weighted by the proportion of total monitor units delivered in each control point to the total monitor units delivered in the plan.

Figure 7:
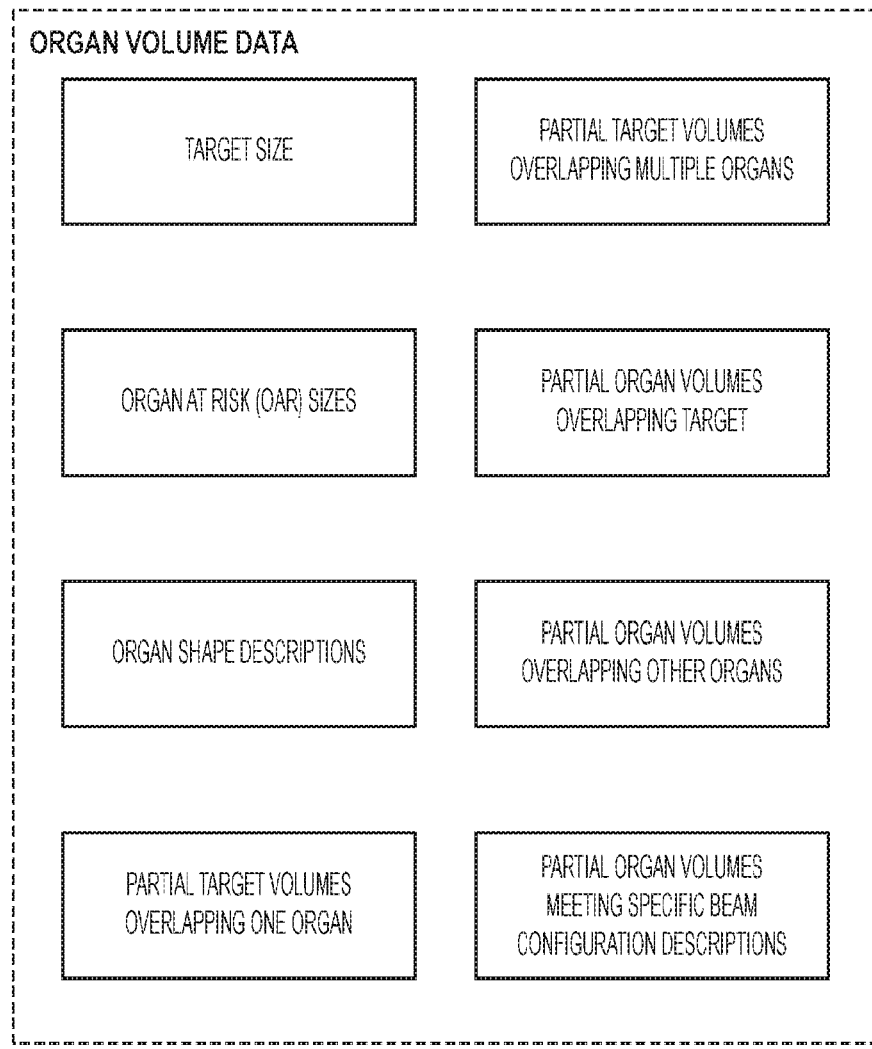
FIG. 7 depicts the contents of organ volume data, as shown in FIG. 6, in accordance with an embodiment of the invention.

Referring to FIG. 7, organ volume data may include any metric useful to an expert practitioner for characterizing a patient's organ volume. In the illustrative example, organ volume data includes target size, organ at risk sizes, organ shape descriptions, partial target volumes overlapping one organ, partial target volumes overlapping multiple organs, partial organ volumes overlapping target, partial organ volumes overlapping other organs, and partial organ volumes meeting specific beam configuration descriptions. In some embodiments organ volume data may include any or all of Gross Tumor Volume to critical organs, organ type (e.g. serial vs. parallel), and dose constraints. In some embodiments the passing rate is calculated in a phantom and organ data is not needed.

Figure 8:
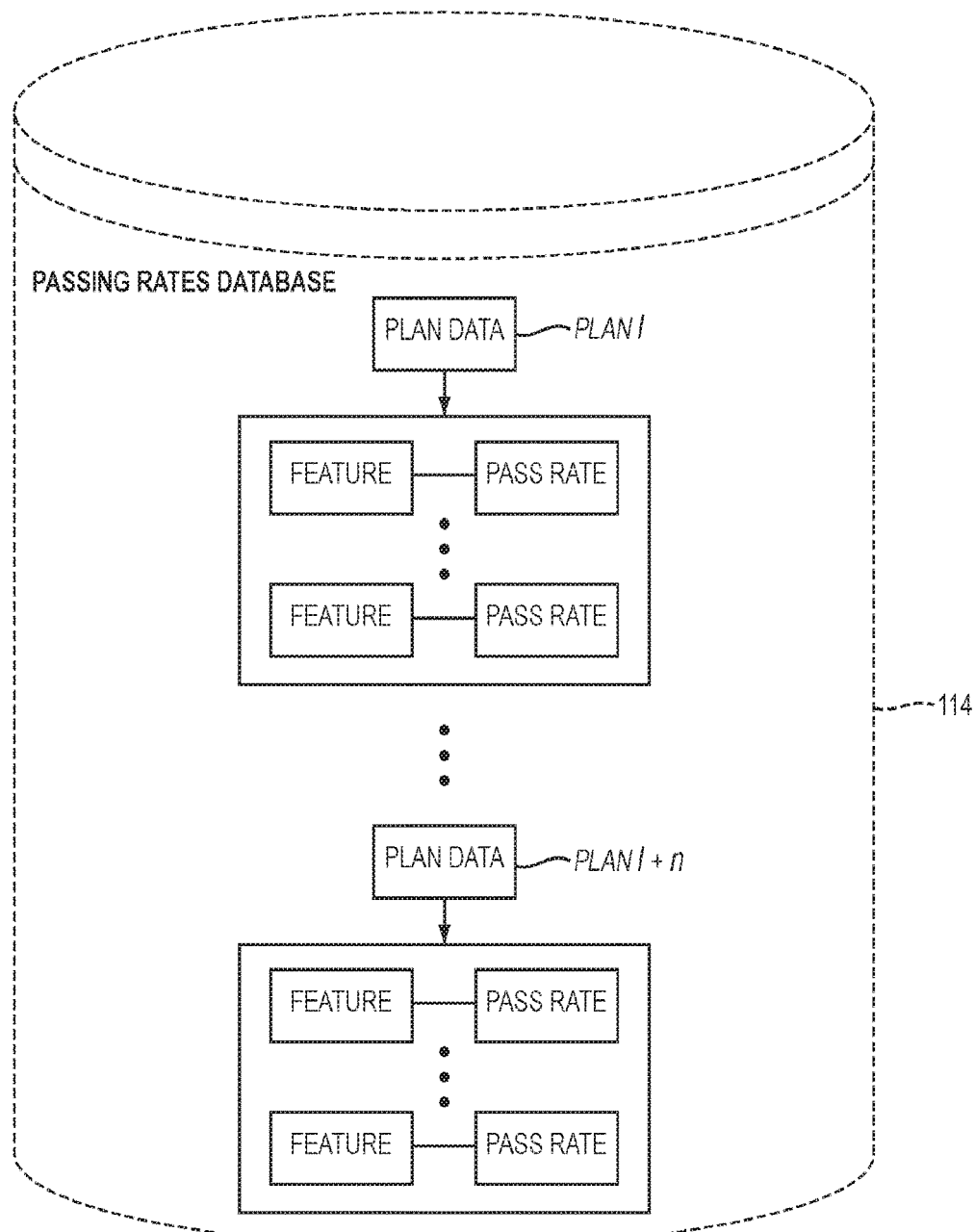
FIG. 8 depicts a block diagram of the salient data stored in the passing rates database, as shown in FIG. 3, in accordance with an embodiment of the invention.

Referring to FIG. 8, passing rate database 114 may include pass rate information for one or more features associated with a patient plan in plan database 112. In some embodiments pass rate data is provided in the passing rate database 114 for each of the plans in plan database 112. In some embodiments pass rate data may have been generated a posteriori from linacs log files. In other embodiments pass rate data may have been generated a priori from conventional QA approach of measuring the linacs on one or more detectors and determining the pass rate. For example, a conventional QA approach may include a 2-dimensional transmission detector to provide a 2-dimensional map of measurements on a plane orthogonal to the beam direction, for example a device made up of a 2-D array of 1024 ionization chambers may be arranged in a regular matrix of 32×32 pixels. In some conventional QA approaches the 2D detector is positioned in between the patient and the MLC. In other conventional QA approaches measurements are performed without patient and the 2D detector can be positioned at the patient's position. Any or all of these measurements may be used to populate the passing rate database 114.

In some embodiments pass rate data may include a combination of a posteriori and a priori data. Pass rate data may refer to any calculation used to compare the program plan beam characteristics with the actual beam characteristics delivered (e.g. in the case of log file data) or to be delivered (e.g. in the case of conventional QA data). In some embodiments pass rate data may include dose difference of a particular point, in other embodiments pass rate data may include distance to agreement (DTA). Preferably, pass rate data include gamma-passing rate data.

In an embodiment, a machine learning model 116 is an algorithm that predicts a priori Intensity Modulation Radiation Therapy (IMRT) Quality Assurance passing rates (e.g. virtual IMRT QA). When planning a radiation treatment for a specific patient the radiation passing rates may be measured to within a certain percent/distance standard (e.g. 2 p/2 mm (i.e., 2%/2 mm) "distance to agreement" or DTA). In some embodiments a method of the invention uses metrics to identify failure modes between the treatment planning system and the delivery of the plans on the Linac (linear accelerator) platforms. In some embodiments a failure mode is less than 90% of plans pass 3%/3 mm DTA criteria. In some embodiments a failure mode is less than 97%, 95%, 92%, 87%, or 85% of plans pass 3%/3 mm DTA criteria. In some embodiments a failure mode is less than 90% of plans pass 2%/2 mm DTA criteria. In some embodiments a failure mode is less than 97%, 95%, 92%, 87%, or 85% of plans pass 2%/2 mm DTA criteria. In some embodiments all or a subset of 37 metrics are considered. In some embodiments the model includes a recognized characteristic, for example that the failing points followed a Poisson-like distribution. In some embodiments a model according to the invention may also include a Synthetic Minority Oversampling Technique (SMOTE) that considerably improves the accuracy of the algorithm.

In some embodiments plan data and pass rate data may be organized in a manner other than in separate databases (e.g. in a single database, or in further subdivided into greater than two databases).

In some embodiments the method includes the following:
Build a database of treatment plans.
Collect gamma-passing rates for each of the plans.
Extract features associated with failure modes between the treatment planning system and the Linacs.
Build a model using Machine Learning that predicts passing rates.

In some embodiments, failure modes may refer to one or more of plan data. In some embodiments certain plan data may result in a failure mode. Plan data that may result in failure modes include, but are not limited to, MLC leafs' transmission; leaf end leakage; jaws' transmission; tongue and groove effect; and dose calculation algorithm. In some embodiments, failure modes may include one or more of modulation factor (e.g. overall complexity), small aperture score 10 mm (DLG, Dose Algorithm); weighted average irregularity factor (tongue and groove); fractional area out of 20×20 box (flatness); and small aperture score 20 mm (DLG, Dose Algorithm). In some embodiments plan database 112 includes modulation factor (e.g. overall complexity), small aperture score 10 mm (DLG, Dose Algorithm); weighted average irregularity factor (tongue and groove); fractional area out of 20×20 box (flatness); and small aperture score 20 mm (DLG, Dose Algorithm).

The IMRT QA method takes several hours and uses up Linac machine life. Thus, some advantageous embodiments of the current invention provide an accurate, fast "off-line" method to determine passing rates.

In some embodiments the method is automated. A benefit of some embodiments of the invention is that it could be an important step in enabling Adaptive Radiation Therapy. Adaptive Radiation Therapy may be the next step in the evolution of IGRT and IMRT, where new IMRT treatment plans are created every 1 to 5 fractions. In order for Adaptive Therapy to be used clinically, IMRT QA must be automated. A benefit of Adaptive Radiation Therapy may be better patient outcomes.

In some embodiments a method of the invention may allow more patients to be treated by increasing the life expectancy of a machine. In some embodiments a method of the invention may allow more patients to be treated by increasing patient throughput.

In some embodiments a method of the invention could save replans.

In some embodiments a method of the invention could save on the cost of QA (for example, an estimate might be a savings of about a few hundred dollars per patient).

The present invention is intended to be used with a radiation therapy apparatus. In one embodiment a radiation therapy apparatus delivers high energy x-ray from an isocentric gantry linear accelerator. In one embodiment a radiation therapy apparatus comprises an IMRT apparatus wherein the beam modulation is accomplished by means of a multi leaf collimator (MLC) or by jaws.

In some embodiments, the systems and methods of the present invention include a machine-learning algorithm (ML) that may be trained to learn the relationship between plan characteristics and passing rates. A generalized linear model (GLM) using Poisson Regression with Lasso regularization may be used to model the failure rate (100−passing rate)[25, 26]. Furthermore, this algorithm may be selected because of its capability to accommodate highly correlated feature sets[25, 26].

Briefly, using Poisson Regression with Lasso regularization the failing rate may be modeled as:

$$\text{Failing Rate}=100-\text{passing rate}=e^{x\beta^T} \quad (I)$$

where x is a 79 dimensional vector, $(1, x_1, x_2 \ldots x_{78})$, and each component (except 1) represents one of the complexity metrics. $\beta^T$ is the transpose of a constant vector with the same dimensions as x. β may be estimated as the constant vector that will maximize the conditional probability of obtaining β giving our dataset of failing rates and complexity metrics. Laplace prior (Lasso) regularization has been assumed for β to limit the complexity of the model, perform feature selection and to follow Occam's razor principle that establishes that the most plausible model is the simplest one. In the present application, simplicity may be measured by the number of components equal to 0 in the estimated β. It is important to highlight that Lasso regularization performs feature selection by driving the components of the vector β that correspond to redundant or unimportant complexity metrics to 0 and effectively eliminating them in the model through the multiplication of the vectors $\beta^T$ with the vector x. In Poisson Regression with Lasso Regularization, β is estimated ($\hat{\beta}$) by solving the following convex optimization problem:

$$\operatorname{argmin}_\beta \text{Loss}(\beta|D) = \operatorname{argmin}_\beta [-\Sigma_{j=1}^n (y_j x_j \beta^T - e^{x_j \beta^T}) + \lambda |\beta|] \quad (II)$$

where D represents the dataset under analysis: the pair of all complexity metrics of a given plan j $(x_j)$ and the failing rate given by $y_j$. The summation in equation II is over all plans that may be included in the training set. λ is a constant that governs complexity and it may be selected as explained below. The higher the value λ, the more components with value 0 the estimated $\hat{\beta}$ will have and the fewer complexity metrics will be used in the model. Once the $\hat{\beta}$ that minimizes equation II is determined, then for any arbitrary plan, equation I can be used to calculate its failing rate given its characteristics.

Overfitting of data using a highly complex model may result in poor performance of an algorithm on out-of-sample data (data that the algorithm has not seen). As such, it may be important to control the complexity of a model. In the present invention, the parameter λ controls the complexity. In a process similar to that of human intuition, the value of λ obtained using cross validation dictates which components of the estimated vector $\hat{\beta}$ are different from 0 and as such, which complexity metrics are included in the model.

If λ is too small, the term λ|β| may be less important and more metrics may be accepted, resulting in a complex model that over fits the data and will be less capable of predicting future IMRT QA passing results.

If λ is too large, all components of the vector $\hat{\beta}$ will be set to 0, and the model will fail to select any complexity metrics and will not explain the data.

In the present invention, the smallest value of λ may be sought that will reduce all components of the vector β to 0 (max Lambda) and the maximum value of λ may be sought that will not set any component to 0 (min Lambda). Then, 100 values may be generated linearly on the log scale and 100 different $\hat{\beta}$ may be obtained by minimizing equation II for each λ. The smallest λ within 1 standard deviation of the λ that minimizes a leave-one-out cross validation (LOOCV) error may be chosen to maximize the generalization capability of the algorithm of the invention, and the final $\hat{\beta}$ may be estimated using that λ. In order to perform LOOCV, a point may be set aside and the model may be constructed using equations I and II. Once the optimal β is determined ($\hat{\beta}$), then the complexity metrics of the plans are used together with equation I to determine the failing rate of the point set aside. This process may be repeated for all points in the dataset.

In order to test the performance of the algorithm of the invention, a LOOCV over the whole dataset and/or a double leave-one-out experiment may be performed. In the latter, a data point may be put aside and an additional LOOCV may be performed over the n−1 dataset to select the λ hyperparameter. The λ obtained in this manner may be used to determine the β coefficients using the n−1 training set, and this model may be subsequently used to predict the sample left out at the beginning. This process may be repeated for each individual sample of the dataset. In that case, λ is not determined using information from the point set aside.

Figure 9:
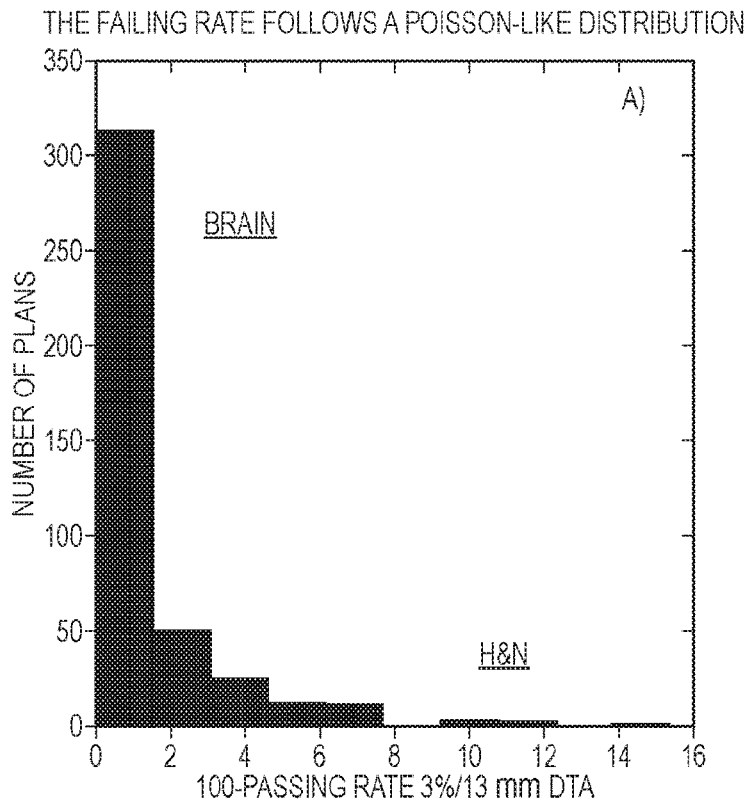
FIG. 9 depicts a histogram showing the measurement/plan failing rate for plans in the study where the failing rate was determined by 100-3%/3 mm passing rate.
Figure 10:
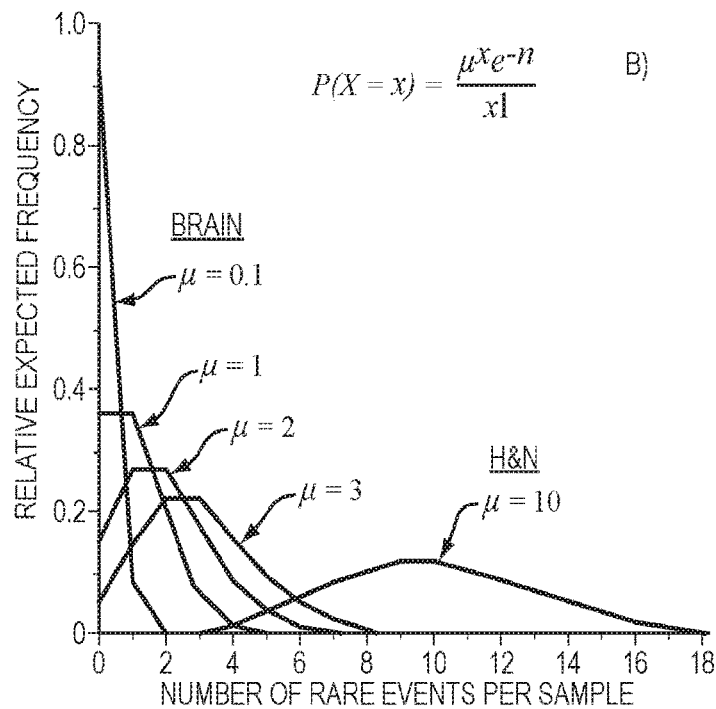
FIG. 10 depicts a Poisson distribution for different means, which demonstrates that plans with high passing rates are characterized by Poisson distributions with small mean values while those with low passing rates are characterized by high mean values.

Among all possible GLMs, a Poisson regression model may be used to model the DTA failure rate. Several reasons led to this choice of model. First, the failure rate is always a positive number skewed towards 0 and high failure rates are rare events. The probability of failure of each diode within a detector array (e.g., a MapCheck 2 detector array) is small and there are a large number of diodes used in determining the passing rate. Predicting failure rate is a count problem, specifically the fraction of diodes that fail out of all diodes considered (those receiving at least 10% of the maximum dose). Counting or rate problems may be modeled using a Poisson regression[27]. FIGS. 9 and 10 illustrate why a Poisson distribution provides a good fit to failure rates. As noted, plans with high passing rates are characterized by Poisson distributions with small mean values while those with low passing rates are characterized by high mean values.

The values of each coefficient can be obtained either by modeling the number of diodes that fail the passing rate and normalizing them by the area of the plan (usually referred as an Offset Poisson distribution), or by modeling the gamma passing rates directly as a Poisson distribution (explained above). In general, the Offset Poisson distribution may be considered to be more accurate, as the number of detectors and not the passing rate may be an integer number.

The methods and algorithms of the invention may be enclosed in a controller or processor. However, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a," "an," and "the" are not limited to one element but instead should be read as meaning "at least one."

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The following examples describe the invention in further detail. These examples are provided for illustrative purposes only, and should in no way be considered as limiting the invention.

EXAMPLES

Example 1

Figure 2:
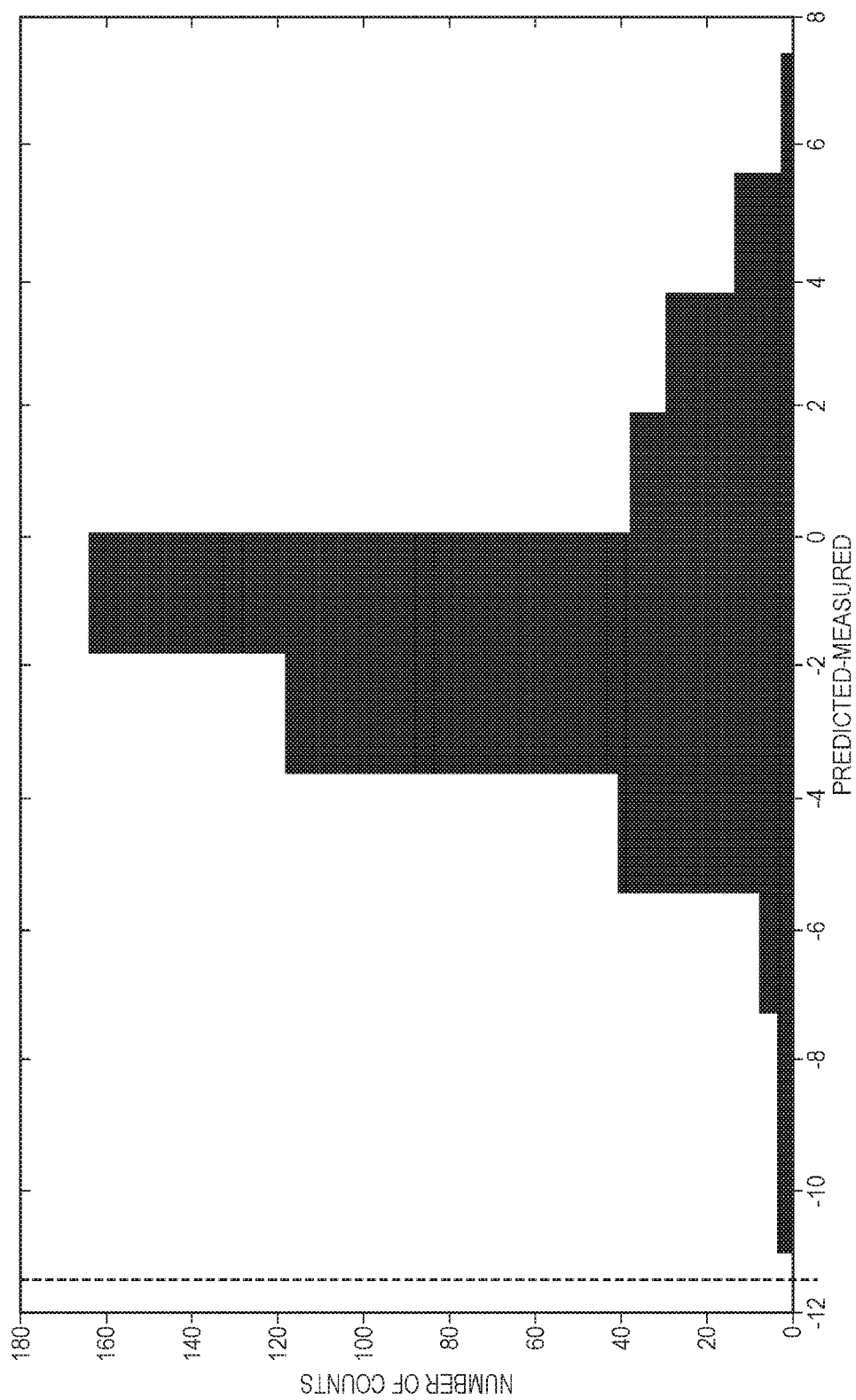
FIG. 2 is a bar graph showing the residual errors of predicted minus measured values of 2 p/2 mm DTA passing rates for 498 IMRT plans using a method in accordance with an embodiment of the invention.

An Algorithm that Predicts a Priori IMRT QA Passing Rates was Developed Using Machine Learning With reference to FIG. 1 and FIG. 2, 498 IMRT plans from all treatment sites were planned in Eclipse, Varian Inc, Palo Alto and delivered using a dynamic sliding window technique on two linac platforms (Clinac iX and TrueBeam, Varian Medical Systems, Palo Alto, Calif.), IMRT QA passing rates were measured and recorded using Mapcheck, Sun Nuclear, Melbourne, Fla. Both, 3 percent 3 mm distance to agreement (3 p/3 mm DTA) and 2 percent 2 mm distance to agreement passing rates (2 p/2 mm DTA) were recorded. Four failure modes between the treatment planning system and delivery of the plans on the Linacs were identified: multi-leaf collimator (MLC) leafs' transmission, leaf end leakage, jaw's transmission and the tongue and groove effect. 37 different metrics were defined to characterize these failure modes. Geometrical features as well as those features weighted by the monitor units were included. A machine-learning algorithm (MLA) was trained to learn the relation between the plan characteristics and the passing rates. Specifically, a generalized linear model with a Lasso selection method was used. The minimization of the cross-validated deviance was used to choose the model hyper parameters. Several distributions were tested but a key observation to learning the relationship between the passing rate and the characteristics of the plans was that the percent of failing points followed a Poisson-like distribution. Additionally, a Synthetic Minority Oversampling Technique (SMOTE) was used to be able to appropriately learn those plans with 2 p/2 mm DTA passing rates smaller than 90%. The use of SMOTE was another key observation and considerably improved the accuracy of the algorithm.

Results: 3 p/3 mm DTA predicted passing rates were found to be within 3% of the measured passing rates for 98% of plans. For the rest 2% of the plans, the predicted and measured passing rates where within 5%. FIG. 1 shows a histogram of the residual errors between predicted and measured 3 p/3 mm DTA passing rates. Additionally, FIG. 2 shows a histogram of the residual errors of predicted vs. measured 2 p/2 mm DTA passing rates. 96% percent of plans were successfully predicted with an error smaller than 5%.

Conclusion: Patient specific IMRT QA passing rates could be accurately predicted a priori using a method that we call virtual IMRT QA. Our models, together with the use of Log Files analysis, independent dose calculations and Quality Assurance of the Linacs could be used to replace current measurement-based IMRT QR methods and improve efficiency and predictability. Additionally, our models could also be used by Planning Systems to improve the deliverability of their plans and produce outcomes with smaller errors.

Example 2

A Framework for Virtual IMRT QA Using Machine Learning

A dataset of IMRT plans were processed using the above-referenced algorithm.

498 IMRT plans from all treatment sites were planned in Eclipse version 11 and delivered using a dynamic sliding window technique on Clinac iX or TrueBeam linacs. 3%/3 mm local dose/distance to agreement (DTA) were recorded using a commercial 2D diode array. Each plan was characterized by 78 metrics that describe different aspects of their complexity that could lead to disagreements between the calculated and measured dose. A Poisson regression with Lasso regularization was trained to learn the relation between the plan characteristics and each passing rate.

As described herein, passing rates 3%/3 mm local dose/DTA can be predicted with an error smaller than 3% for all plans analyzed. The most important metrics to describe the passing rates were determined to be the MU factor (MU per Gy), small aperture score (SAS), irregularity factor and fraction of the plan delivered at the corners of a 40×40 cm field. The higher the value of these metrics, the worse the passing rates.

Accordingly, the Virtual QA process of the invention predicts IMRT passing rates with a high likelihood, allows the detection of failures due to set up errors, and is sensitive enough to detect small differences between matched linacs.

Dataset. 498 IMRT plans from multiple treatment sites were planned using Eclipse version 11 (Varian Medical Systems, Palo Alto, Calif.) and delivered using a dynamic sliding window technique on either TrueBeam (HD MLCs) or one of our four nominally matched Clinac iX linacs with millennium MLCs (Varian Medical Systems, Palo Alto, Calif.). All plans were clinical plans used to treat patients at our institution. The Clinac selected for IMRT QA delivery was chosen randomly in each case depending on the unit that finished treatment first on any given day. 416 plans used 6 MV (6×) only, 32 plans used 15 MV only (15×), and 50 plans were mixed energy (mixed). The IMRT QA measurements were performed as part of a clinical routine using Mapcheck2 with the SNC software version 6.1 (Sun Nuclear, Melbourne, Fla.) with measurement uncertainty turned off. The Mapcheck was set up on the couch with 3 cm of solid water on top and the gantry angle overridden (delivery was always performed at 0° gantry angle) but collimation rotation allowed. Every day before IMRT QA delivery, dose calibration was verified for a 100 MU, 10×10 cm reference field and recalibrated if there was a disagreement larger than 0.5% in absolute dose on the central axis (CAX). Only points with doses greater than 10% of the global maximum dose per plan were included in the analysis. Composite Local 3% Dose/3 mm distance to agreement (DTA) passing rate was recorded for all plans and stored in a Redcap database (Harvard Catalyst, Boston, Mass.).

Feature extraction and complexity metrics. Five main sources of errors that could lead to disagreement between the treatment planning system and delivery of the plans were identified: MLC leaf transmission, leaf end leakage (Dosimetric Leaf Gap, DLG), transmission through the jaws, tongue and groove effect, and charged particle equilibrium failure. For each plan, 78 different complexity metrics (referred also as features) were defined to characterize these categories. Plans were characterized using aperture-based complexity metrics based on the MLC leaf positions and fractional monitor units delivered per control point. Without being limited to any one theory, it is believed that aperture-based complexity metrics are more direct descriptors of the five main sources of discrepancies described above than fluence-based complexity metrics as they represent the delivery parameters utilized by the treatment machine and as such may offer better insight into the disagreement between the calculated and measured dose. Geometrical complexity metrics as well as those weighted by the fractional monitor units for each aperture were included. Complexity metrics were computed as the average over all control points and beams or as the average of the complete irradiated area outline (CIAO). In some cases, the maximum and minimum value of the complexity metric for a given beam of the respective plan was also included. In general, these complexity metrics (features) are: the fraction of MUs per dose delivered, energy, type of Linac, jaw position, collimator angle, distribution of MLC leaf pair gaps (up to the fifth moment of the distribution), ratio of the area of MLC within the jaws aperture, area, perimeter, aperture irregularity as defined by Du et al.[16], fraction of the area of the plan delivered within circles of different radii centered at isocenter (5,10,20 cm), fraction of MLC leaf gaps with an opening smaller than a certain value average over all beams and control points: 2 mm, 5 mm, 10 mm, 20 mm and (Small Aperture Score, SAS, as defined by Crowe et al[20]) or the maximum value of those for a given beam of the plan (only averaged over the control points), and the fraction of area receiving dose through the jaws and fractional area receiving dose from different number of beams. Before being used in the algorithm, complexity metrics were rescaled using their mean values and normalized by their standard deviations. Additionally, the effect of MLC speed was modeled by dividing each opposing MLC gap by the monitor units of that control point and then averaging these values over all control points and all beams for a given plan. This metric was not selected by the algorithm and as it did not improve the accuracy, and therefore the effect of MLC speed is not discussed further.

Plan visualization. As each plan is characterized by a vector of 78 complexity metrics, direct visualization of the effect of different metrics on the passing rates is prohibitive. Therefore, a principal component analysis (PCA) was developed to find the dimensions where the complexity metrics have the biggest variance[24]. PCA performs this task by finding the dimensions or orthogonal base (vectors) on which if every vector x is projected from the feature space matrix X, the variance of the final components of each vector is maximized. Each of these dimensions is found as a linear combination of the initial complexity metrics (features). PCA then, transform the vectors X into this orthogonal base. This allows the mapping of a high dimensional vector such as the complexity metrics to a smaller dimensional space. By selecting the first two dimensions, (the two dimensions with the highest variance), a representation of a high dimensional vector can be performed in a 2D plane.

In the present example, the first two dimensions of vectors following a PCA transformation were used to graph the distribution of plans on a 2D map. Visual inspection of low passing rates plan clustering was performed as a verification of accurate plan characterization by the complexity metrics. In addition to dimensionality reduction, PCA is also used for feature selection because redundant complexity metrics can be eliminated. The tradeoff, however, is that interpretation of the relevant feature is lost because the final complexity metrics are linear combinations of the initial metrics. Therefore, in the present example another method is used to perform feature selection. This method keeps the interpretation of the complexity metrics intact but is not affected by redundant complexity metrics. PCA is not necessary beyond graphical representation of the plans.

Error handling and re-delivery. In a database of 498 IMRT plans, some setup errors, faulty dose calibration of the Mapcheck device or other unidentified errors were expected. In evaluating the data, therefore, if a plan disagreed by more than 3% using the local 3% dose/3 mm DTA predicted value, the plan was re-delivered and re-measured. The results following redelivery were inserted back into the database. These plans were then represented by two observations in the database. In case the difference between the measurement value on the dataset and the re-delivered value was larger than 5%, the initial value was considered in error and replaced (these plans were redelivered multiple times to verify that the initial value was indeed in error). Conversely, if the new measurement was within 5% of that in the database, the new value was entered as an independent measurement without changing the initial value. In total, 43 plans were redelivered.

Results

Figure 11:
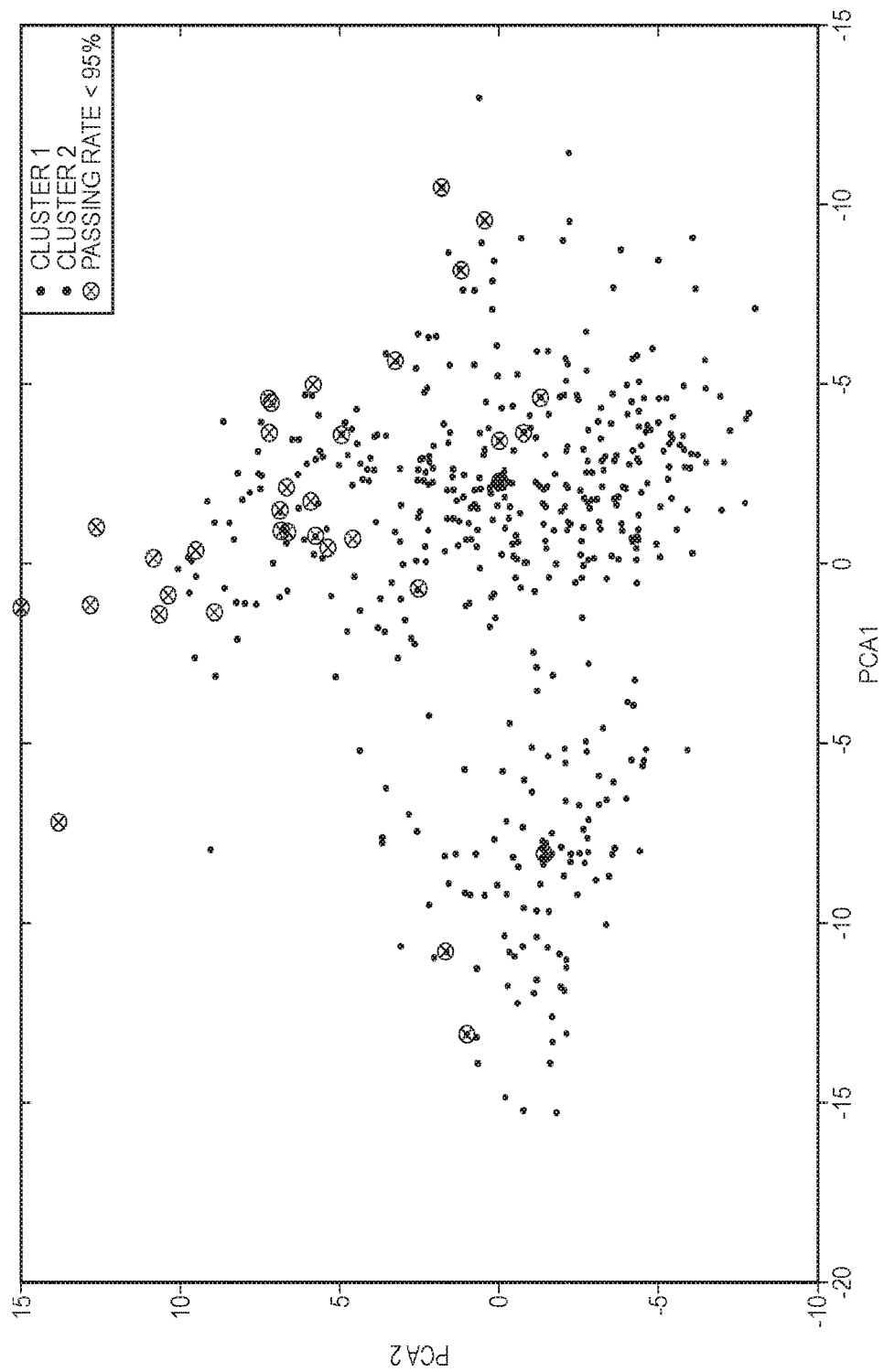
FIG. 11 depicts the clustering of plans with low passing rates along the dimensions PCA 1 and PCA 2. A hierarchical clustering has been used to enhance the visualization representation. Plans with passing rates less than 95% tend to cluster in the center of the plane. In other dimensions, different patters can be observed.

Visualization. In order to investigate whether complexity metrics that we extracted were describing passing rates, the principal components of our dataset were obtained. Out of the initial 78 complexity metrics, 21 dimensions retain 95% of the complexity metrics' variance and the first 4 principal components retain 69.67%. FIG. 11 shows a schematic representation of the plans on the plane defined by PCA 1 vs PCA 2 (similar results are observed with other principal components). As can be observed, plans with passing rates smaller than 95% seem to cluster in the region of the space where PCA 1 is higher than 0 and PCA 2 is higher than 5, providing confidence that our complexity metrics are describing plan passing rates.

Figure 12:
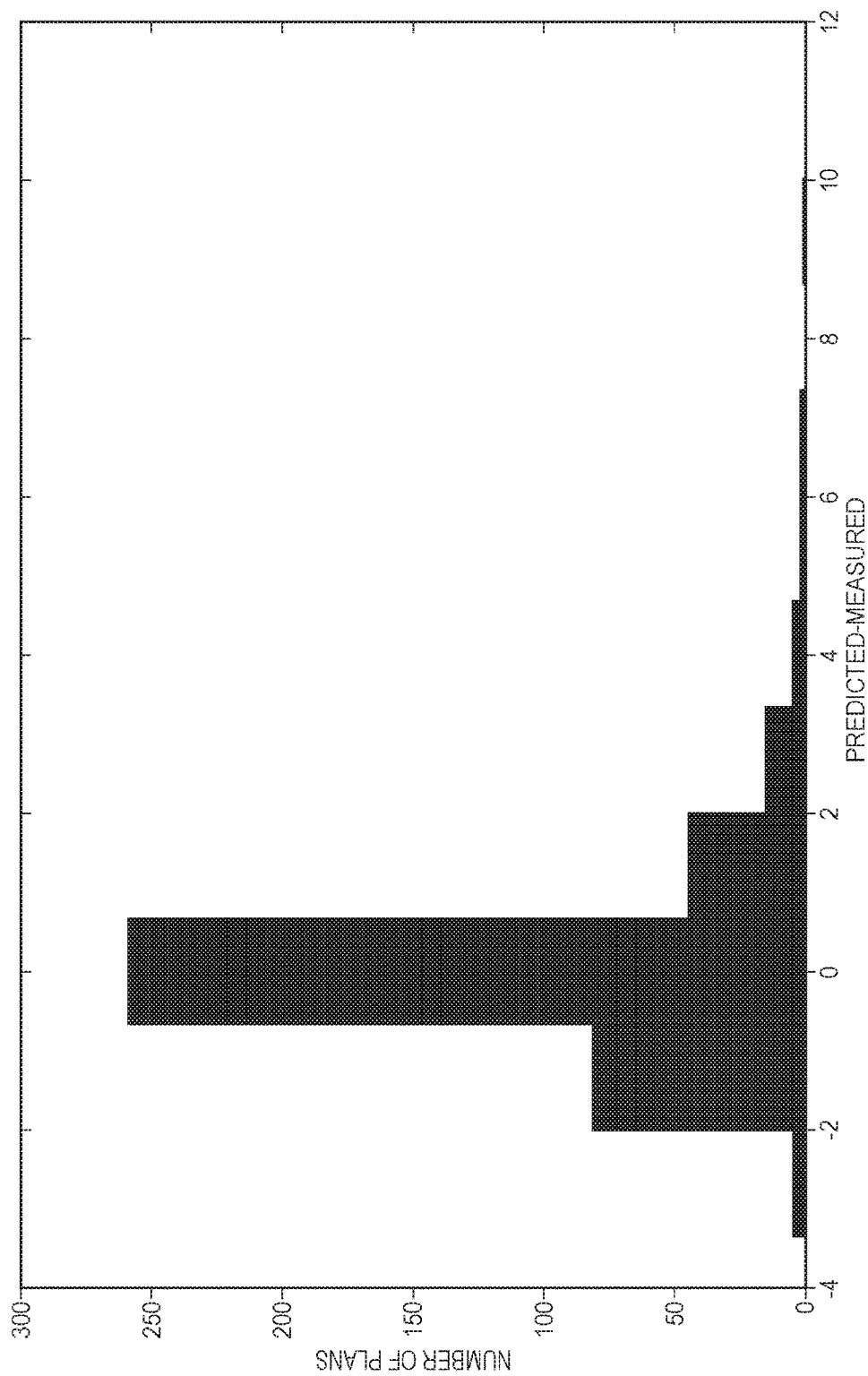
FIG. 12 is a bar graph showing the residual errors of predicted minus measured values for a model described in Example 2.
Figure 13:
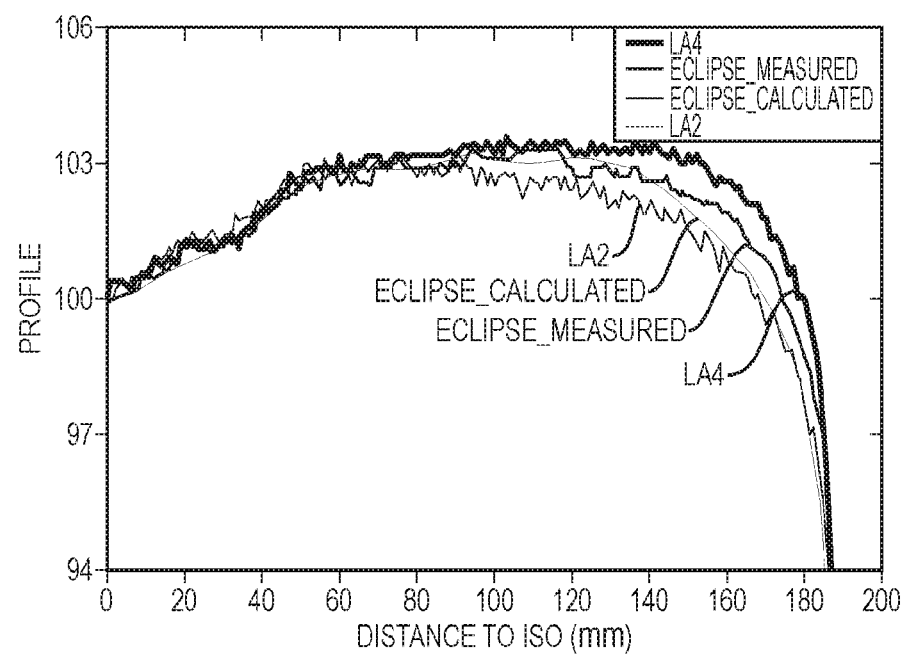
FIG. 13 is a diagonal profile of Clinac 4 (LA4) as an example of all the clinacs compared to the profile of Clinac 2 (LA2) and the measured and calculated profile from Eclipse.

Exploration. A model incorporating all data points was initially constructed. The lambda that minimized the LOOCV error was $\lambda_{min}$=0.0128, which resulted in 35 degrees of freedom (number of complexity metrics selected) explaining 76.01% of the variance observed in the failing rates. The three most important complexity metrics (the first complexity metrics with coefficients different than 0) were the MU factor (MU per Gy), the MU weighted irregularity factor as described by Du at al[16] and the fraction of MLC segments with opposing leaf gaps smaller than 10 mm (Small Aperture Score, SAS_10 mm). As FIG. 12 shows, "good agreement" between the predicted and the measured failure rate is obtained even in this exploratory model. However, as 14 plans still had residual errors larger than 3%, other complexity metrics selected by the algorithm were looked at as well as those plans that had a disagreement larger than 3% in order to improve the model. In addition to those mentioned above, three other important features were the energy (6MV vs. other energy), the machine/MLC type (Clinacs equipped with a Millennium MLC vs. TrueBeam equipped with an HD-120 MLC), and whether delivery was performed on one specific clinac (Clinac 2). The first two features were expected, and imply that independent models for the machine/MLC type and for each energy should be constructed. The fact that Clinac 2 was an important feature, however, was unexpected as the four clinacs are nominally matched. Further investigation pointed out that plans with a large fraction of the area delivered outside a circle with a radius equal to 15 cm (whole pelvis or three field breast plans) have passing rate of 100% on Clinac 2 but substantially lower passing rates on the other Clinacs inspected. On further inspection it was discovered that off axis profiles for Clinac 2 most closely matched the Eclipse model (FIG. 13). At the corners of the 40×40 cm² field, dose differences larger than 3% between Clinacs 1, 3 and 4 and the Eclipse model can be observed, while almost perfect agreement is obtained for Clinac 2. These results indicated that individual models would need to be constructed for True Beam, Clinac 2, Clinac 1,3,4 and for each energy, respectively. In the present invention, the models for 6 MV plans for each of the Linacs and the TrueBeam are inspected. Models for 15 MeV and mixed energy plans with their particular complexity metrics will be evaluated in a future study, particularly because additional data is needed to properly separate these datasets. Additionally, it was also noted that regardless of the Linac, large field plans where multiple Mapcheck 2 acquisitions are necessary to acquire the full dose distribution may be prone to error and the results might depend on the way they are acquired.

Figure 15:
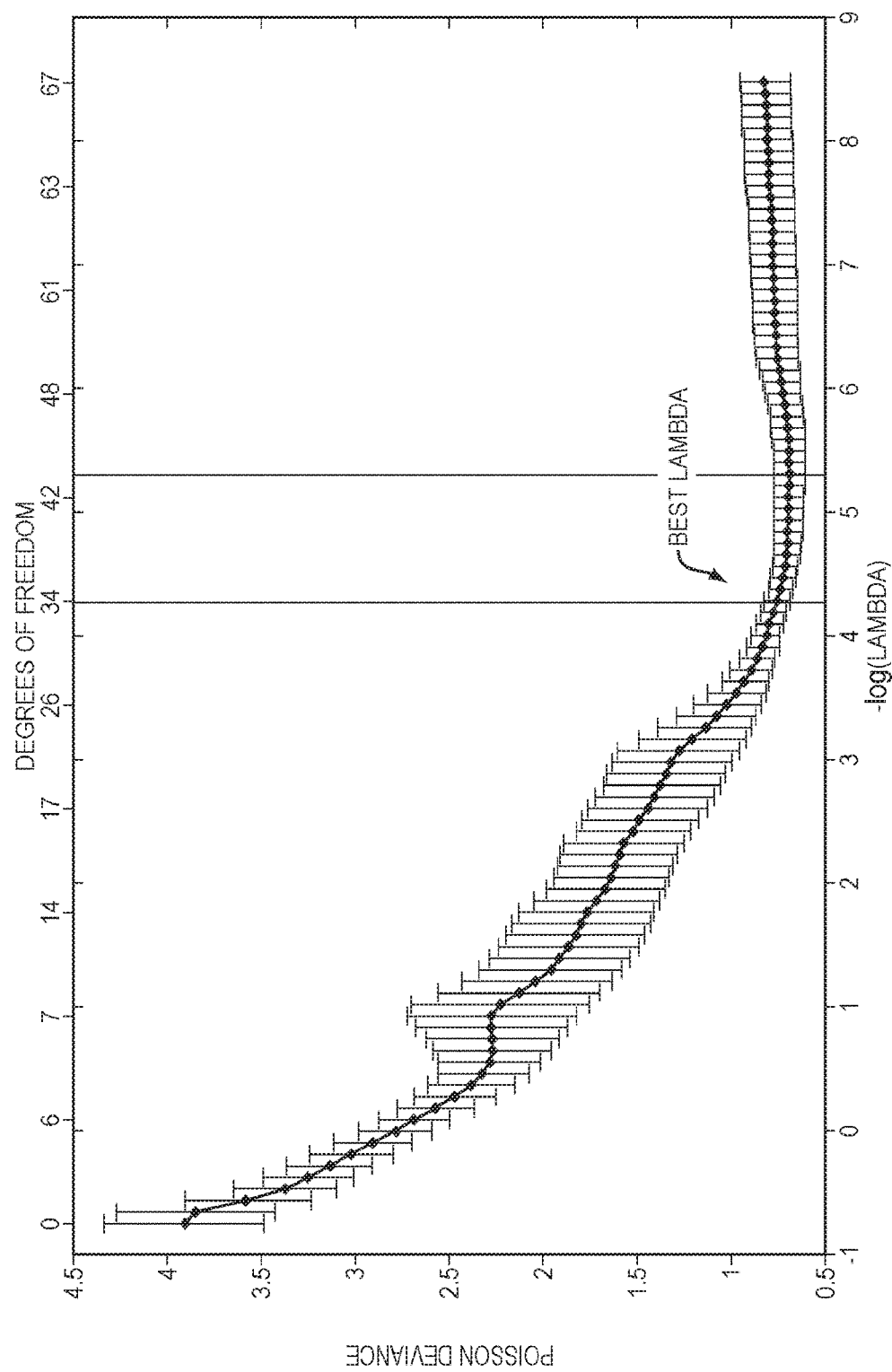
FIG. 15 is a graph depicting a leave-one-out cross validated Poisson deviance for the Clinac 1, 3, and 4 models. The Lambda value one standard deviation from the lambda that minimized the cross validation was selected as the hyper parameter for the model. 35 features out of the initial 78 were selected for this lambda.
Figure 16A:
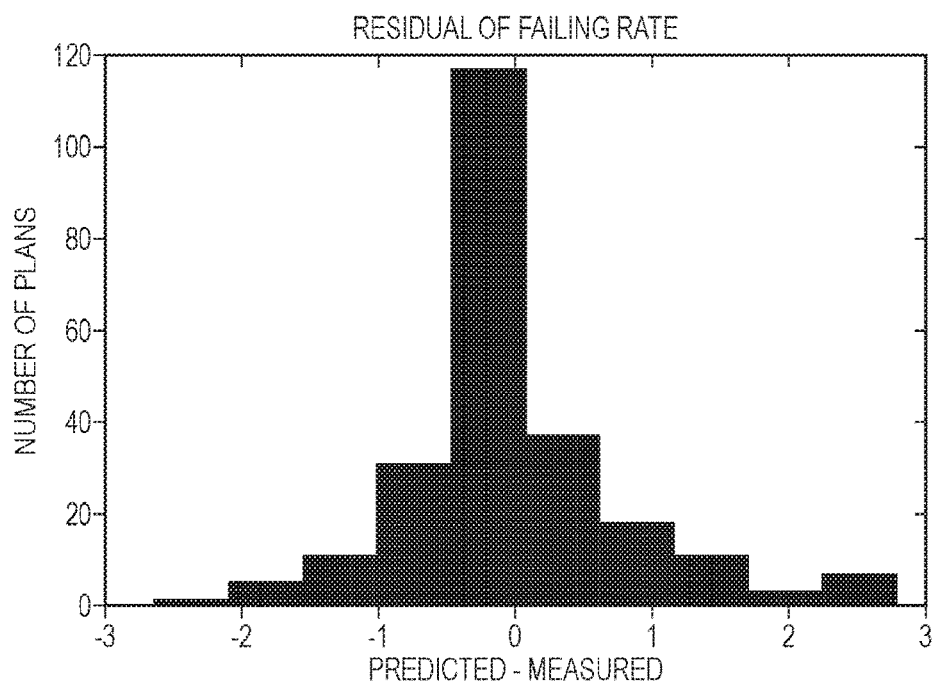
FIGS. 16A and 16B depict bar graphs for the cross-validated residual error for the Clinac 1, 3, and 4 models (FIG. 16A), and the cross validated residual error for the Clinac 2 model (FIG. 16B). In both FIGS. 16A and 16B, a cross-validated residual error smaller than 3% was obtained.
Figure 16B:
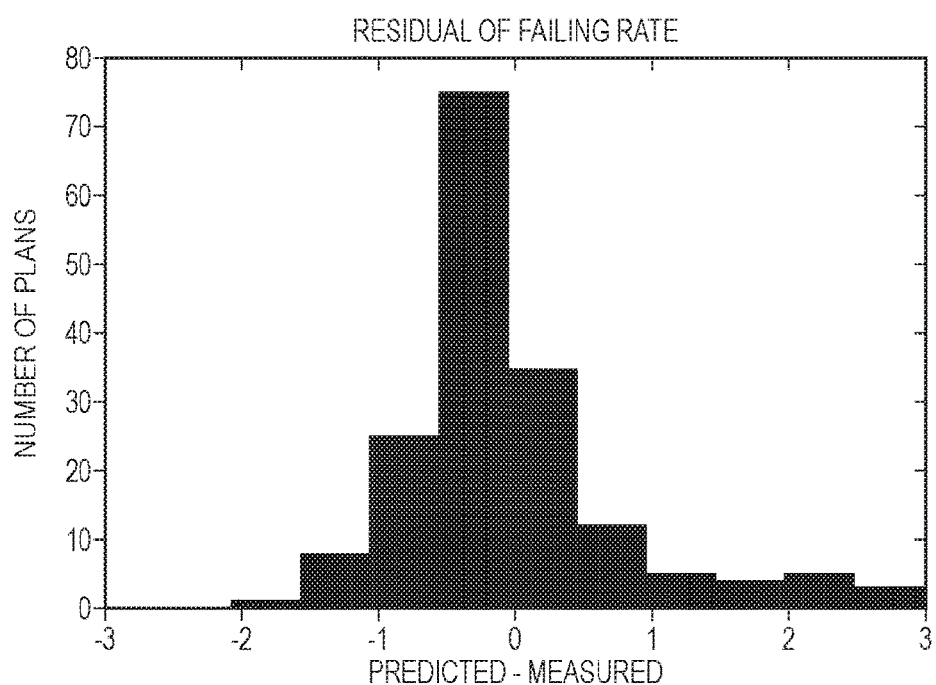

Models for 6 MV plans. 243 plans were delivered on Clinacs 1, 3, and 4, while 176 plans were delivered on Clinac 2 and 21 on TrueBeam. FIG. 15 shows a figure of the cross-validated Poisson deviance vs. the hyper parameter lambda for the 6× model for Clinacs 1, 3 and 4. The largest value of lambda within 1 standard deviation of the lambda that minimizes the cross validation, 0.014 for the Clinacs 1,3,4 model, was chosen as the hyper parameter in order to have a more robust model. 35 complexity metrics were selected to describe the failing rate (their corresponding components of the vector β were not 0), which in this case explains 87% of the observed null deviance with p=5.8*10⁻12, indicating that the current model is significantly better than a null model (explaining the data with a constant value). Similar results were obtained for the models of Clinac 2 and TrueBeam. The 5 most important complexity metrics for each of these models are shown in FIG. 14. It is important to highlight that different models will select different complexity metrics and coefficients, further supporting the position that models need to be constructed for each independent Linac. The TrueBeam is primarily used to treat smaller targets such as those encountered in SBRT. Finally, explaining 87% of the variance of the measured failing rate for Clinacs 1, 3 and 4, is sufficient to predict all plans within a 3% error in a leave-one-out cross validated experiment (FIG. 16A). A similar result is obtained for the Clinac 2 (FIG. 16B) and TrueBeam models (data not shown). This 3% error threshold was sufficient to identify delivery problems in a number of different plans. FIG. 17 shows 5 different plans in which the initial result had a disagreement larger than 3% as compared to the predicted value. On redelivery, all fell within 3% of the model, suggesting a set up or other measurement error during initial delivery.

Figure 18:
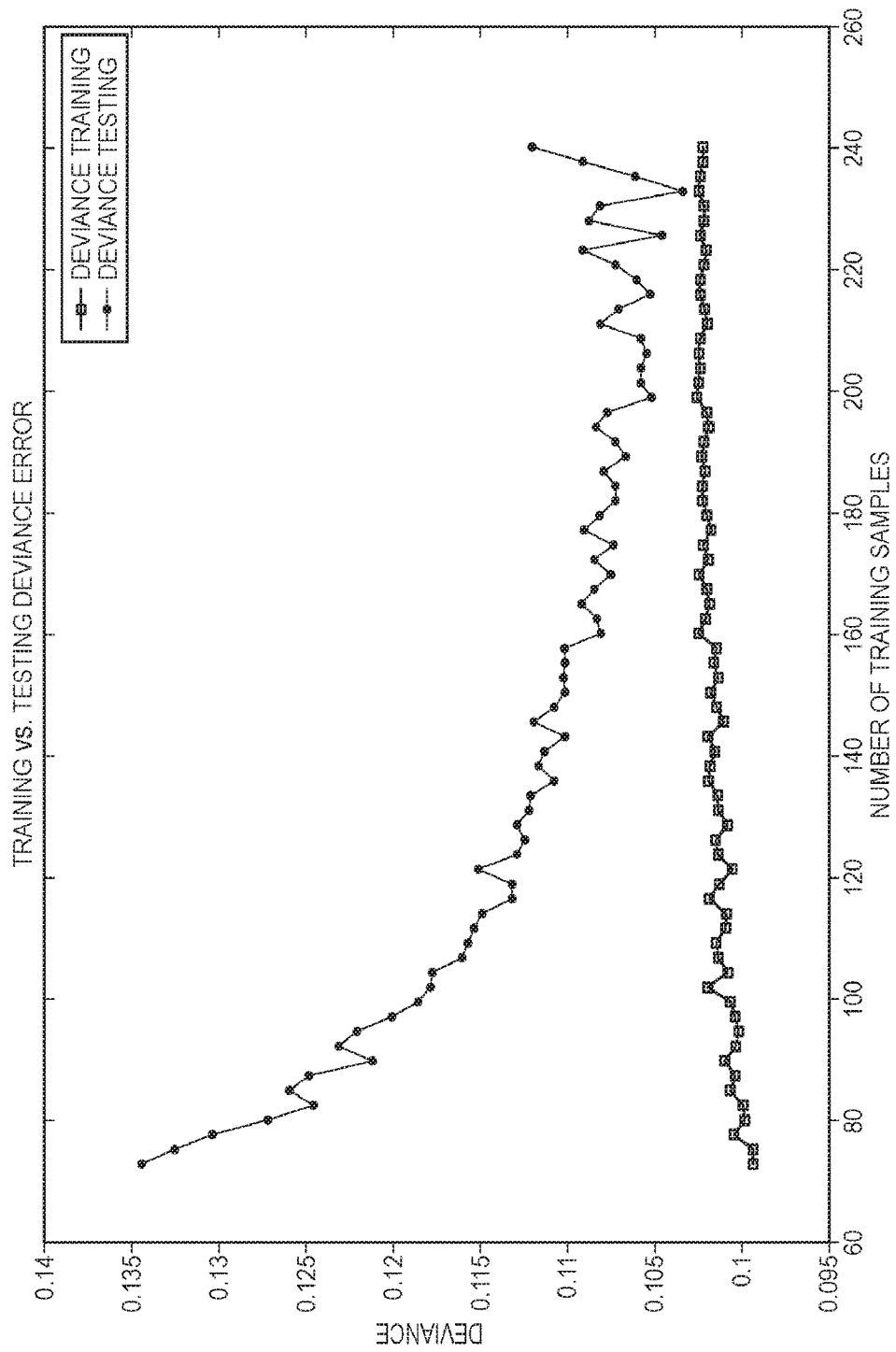
FIG. 18 depicts a learning curve for a model described in Example 2 and deviance of the model on the testing sample and the training sample. Beyond 200 plans, increasing the number of plans in the training sample produces no further improvement in the model.
Figure 19:
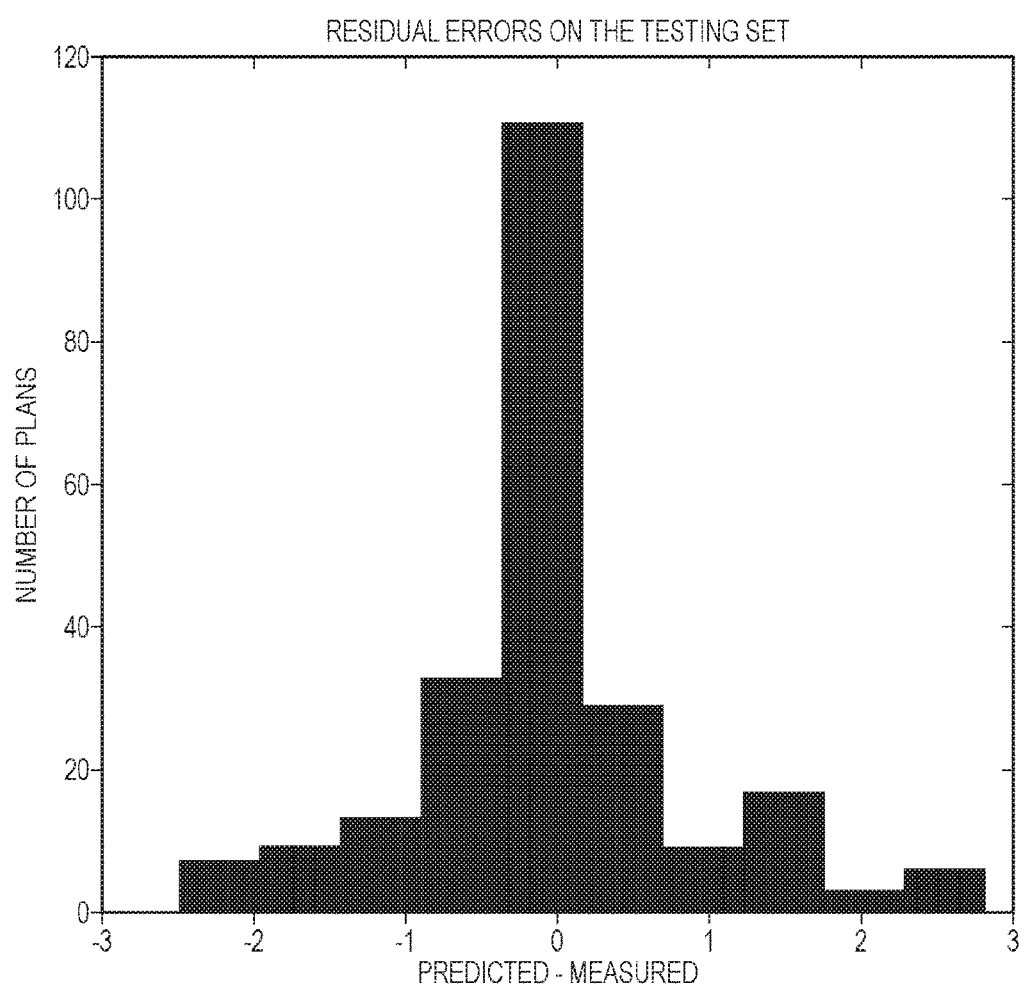
FIG. 19 depicts a bar graph for the residual error of all plans predicted using out of sample data to estimate both lambda and the model coefficients.
Figure 20:
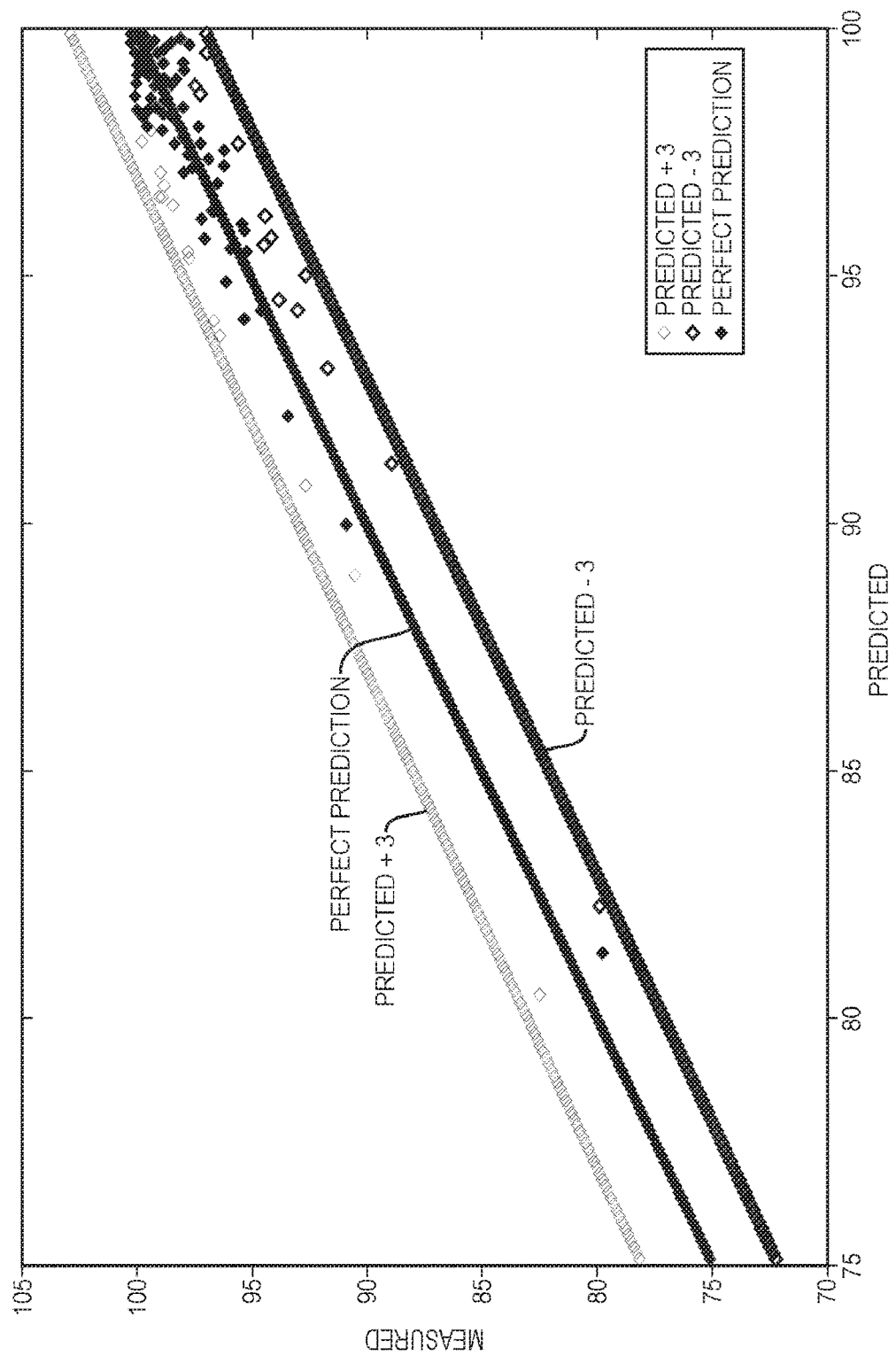
FIG. 20 depicts measured vs. predicted passing rates. All points lay within ±3% of the perfect predicted passing rates (i.e., predicted +3 as compared to a perfect prediction, predicted −3 as compared to a perfect prediction, and a perfect prediction).

Number of plans needed and error on a test set. An important question to answer when a model is constructed is how many plans are needed to generate an accurate model. The answer to this question will generally be model specific. For instance, if different linacs are combined in one model, it is plausible to expect that more plans would be needed due to a higher variance of the data than when only one linac is modeled. FIG. 18 shows a learning curve for Clinac 1, 3 and 4 models where the normalized deviance of the training and testing sets are plotted as a function of the number of plans in the training set. As can be observed, the testing deviance plateaus at approximately 200 plans and no further improvement is obtained by including more plans. Finally, the cross validation error is an estimation of the error that will be made by the algorithm when hyper parameters are selected using the same dataset. This is because the hyper parameter lambda, if chosen using LOOCV, as described herein, contains information about all plans and as such its use in the model can result in an under estimation of the error. In that sense, it is usually recommended the data be split into three sets: the training set to estimate the coefficients of the model, a validation set to estimate the hyper-parameters, and a test set to evaluate the error that the model will make. As shown herein, a double LOOCV was performed as explained above. The residual errors of the algorithm constructed in this manner should be a realistic estimation of the errors that the model will make when predicting plans that have not been included. FIG. 19 shows these residual errors for the Clinac 1, 3 and 4 model. As can be observed, the double leave-one-out error estimation is slightly larger than the cross-validation errors shown in FIG. 15, while still less than 3% for all plans. Finally, a better visualization of the predictive value of the algorithm of the invention is shown in FIG. 20, where the predicted passing rates are plotted against the measured values. A linear regression is obtained, as expected, where the observed dispersion is representative of the intrinsic noise within the measurements that is not explained by the model.

Discussion. As demonstrated herein, it is possible to predict IMRT QA passing rates a posteriori within a 3% error using a Poisson Regression model with Lasso regularization that combines different complexity metrics. This accuracy was shown for Linacs with different underlying behaviors and as a result, different models. In all cases, at least 87% of the variance observed in the passing rates is explained by the models. This is a substantial improvement over current approaches that analyze the correlation between complexity metrics and passing rates individually. Further improvement of the accuracy may be possible by using a zero-inflated Poisson or negative binomial regression model, including quadratic terms, ensemble methods, redelivering plans in order to reduce noise within the existing data (variations on the order of 2% are not uncommon after redelivery of plans) or predicting passing rates for individual beams. However, in certain aspects of the invention, a constant error (3%) around the prediction for all plans as a threshold may be used despite the fact that the error of the prediction, according to a Poisson distribution, is plan specific and depends on the mean value predicted.

Additionally, passing rates have been predicted using aperture-based metrics which allow for easy identification of the different categories leading to disagreement between the treatment planning and delivery platforms. In that sense, important complexity metrics across the different models include: MU factor (a measurement of the overall complexity of the plan), different small aperture scores (DLG modeling), the irregularity factor (tongue and groove modeling), and the fraction of beams delivered outside circles of specific radii (associated with beam profile disagreement).

Plans of varying complexity may tend to have different passing rates. Head and neck plans, for example, are often highly modulated, and lower passing rates are not uncommon. This is reflected in the RPC credentialing results from IMRT irradiation of the head and neck phantom, in which 18.4% of institutions failed to pass a 7% dose/4 mm DTA criteria (considerably less rigorous than that used in the current study); when the criteria were changed to 5% dose/4 mm, more typical of that used in the institutional setting, the failing rate doubled[28]. The Virtual IMRT QA process has the potential to change how IMRT QA is viewed and evaluated. For instance, if after measurement only 89% percent of pixels meet the passing criteria, but the model predicts 90.5%, the result may be considered acceptable.

Patient-specific IMRT measurements may also become an exercise in testing whether delivery systems have deviated from their state at commissioning. The common 90% threshold for determining whether a plan is acceptable is arbitrary, mathematically inaccurate and very inefficient at detecting clinically relevant errors. If a significant clinically relevant threshold is found (which can only be obtained using outcome data), plan specific predictions may be used to detect errors and delivery limitations, not only when this threshold is exceeded, but also when a significant deviation has occurred from the expected value. The virtual IMRT QA approach improves on the current IMRT QA process by providing QA predictions and thresholds for each individual plan (as shown in FIG. 20). Once the dependence of the passing rate on the complexity of the plan has been removed through Virtual IMRT QA, then random noise around that value can be expected. In this sense, the present models are useful in detecting both set up and dose calibration errors, and also in pointing out that the characteristics of one of the Clinacs described herein had different profile characteristics in the outer corners of a 40×40 field.

Virtual IMRT QA may be used to detect clinically relevant errors reported in the literature that have been impossible to detect with the current IMRT QA process and the one fits all 90% threshold approach.

Moreover, knowing that a plan is unlikely to pass would reduce the delays that occur when a plan fails QA. By incorporating Virtual IMRT QA predictions within the optimization process, failing plans may be potentially eliminated. Additionally, different departments will be able to compare the accuracy of their commissioning and TPS data by knowing what passing rate would be obtained for the same plan at a different institution. This may require building models for each combination of equipment or methodology for pre-treatment verification used by different departments or standardizing them across the field. Thus, the present invention may be used to standardize dose delivery accuracy across different institutions by bringing all deliveries within the inaccuracy observed at selected institutions whose commissioning and delivery systems have been carefully verified. In addition, Virtual IMRT QA may be used in adaptive radiation therapy applications, highlighting those plans likely to pass or fail before, and allowing for the QA measurements to be performed after treatment. For example, one Linac may be dedicated to adaptive radiation therapy, and on that Linac, a higher level daily QA would be performed where a set of pre-selected plans (5 or 6) that test the different factors (identified with Virtual IMRT QA) leading to disagreements between TPS and Linac delivery could be measured. Once the pre-treatment measurements for these plans are confirmed within the levels of confidence indicated by Virtual IMRT QA, patients could be treated with plans developed in that session. Virtual IMRT QA could then be used to predict whether these plans would pass QA and accordingly, whether patients could be safely treated. To confirm the prediction of Virtual IMRT QA, the plans used to treat the patients could be measured after treatment.

Conclusions. Virtual IMRT QA is capable of predicting IMRT QA passing rates within 3% for different delivery platforms and with different underlying sources of errors. This process proved to be clinically significant in detecting small set up errors in the measurement process as well as a mismatch of one of four otherwise identical linacs. By providing plan specific thresholds, improved efficiency and reduced re-planning, standards to which departments can compare their results, safe implementation of adaptive radiotherapy and potentially eliminating failing QA altogether, Virtual IMRT QA may have profound implications for the current IMRT QA process.

A number of patent and non-patent publications are cited herein in order to describe the state of the art to which this invention pertains. The entire disclosure of each of these publications is incorporated by reference herein.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. In some embodiments, the terms "about" or "approximate" include ±10% of a dimension, size, formulation, parameter, shape or other quantity or characteristic to which the terms "about" or "approximate" are applied. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All systems and methods described herein that embody the present invention can, in alternate embodiments, be more specifically defined by any of the transitional terms "comprising," "consisting essentially of," and "consisting of."

REFERENCES

[1] G. A. Ezzell, J. M. Galvin, D. Low, J. R. Palta, I. Rosen, M. B. Sharpe, P. Xia, Y. Xiao, L. Xing, C. X. Yu, I. subcommitte, A.R.T. committee, "Guidance document on delivery, treatment planning, and clinical implementation of IMRT: report of the IMRT Subcommittee of the AAPM Radiation Therapy Committee," Med Phys 30, 2089-2115 (2003).

[2] G. A. Ezzell, J. W. Burmeister, N. Dogan, T. J. LoSasso, J. G. Mechalakos, D. Mihailidis, A. Molineu, J. R. Palta, C. R. Ramsey, B. J. Salter, J. Shi, P. Xia, N. J. Yue, Y. Xiao, "IMRT commissioning: multiple institution planning and dosimetry comparisons, a report from AAPM Task Group 119," Med Phys 36, 5359-5373 (2009).

[3] D. A. Low, W. B. Harms, S. Mutic, J. A. Purdy, "A technique for the quantitative evaluation of dose distributions," Med Phys 25, 656-661 (1998).

[4] J. Van Dyk, R. B. Barnett, J. E. Cygler, P. C. Shragge, "Commissioning and quality assurance of treatment planning computers," Int J Radiat Oncol Biol Phys 26, 261-273 (1993).

[5] R. A. Siochi, E. C. Pennington, T. J. Waldron, J. E. Bayouth, "Radiation therapy plan checks in a paperless clinic," J Appl Clin Med Phys 10, 2905 (2009).

[6] B. E. Nelms, M. F. Chan, G. Jarry, M. Lemire, J. Lowden, C. Hampton, V. Feygelman, "Evaluating IMRT and VMAT dose accuracy: practical examples of failure to detect systematic errors when applying a commonly used metric and action levels," Med Phys 40, 111722 (2013).

[7] N. Childress, Q. Chen, Y. Rong, "Parallel/Opposed: IMRT QA using treatment log files is superior to conventional measurement-based method," J Appl Clin Med Phys 16, 5385 (2015).

[8] B. E. Nelms, H. Zhen, W. A. Tome, "Per-beam, planar IMRT QA passing rates do not predict clinically relevant patient dose errors," Med Phys 38, 1037-1044 (2011).

[9] S. Stojadinovic, L. Ouyang, X. Gu, A. Pompoš, Q. Bao, T. D. Solberg, "Breaking bad IMRT QA practice," J Appl Clin Med Phys 16, 154-165 (2015).

[10] G. Palaniswaamy, R. Scott Brame, S. Yaddanapudi, D. Rangaraj, S. Mutic, "A statistical approach to IMRT patient-specific QA," Med Phys 39, 7560-7570 (2012).

[11] G. A. Ezzell, J. W. Burmeister, N. Dogan, T. J. LoSasso, J. G. Mechalakos, D. Mihailidis, A. Molineu, J. R. Palta, C. R. Ramsey, B. J. Salter, J. Shi, P. Xia, N. J. Yue, Y. Xiao, "IMRT commissioning: multiple institution planning and dosimetry comparisons, a report from AAPM Task Group 119," Medical physics 36, 5359-5373 (2009).

[12] M. Nauta, J. E. Villarreal-Barajas, M. Tambasco, "Fractal analysis for assessing the level of modulation of IMRT fields," Med Phys 38, 5385-5393 (2011).

[13] S. Webb, "Use of a quantitative index of beam modulation to characterize dose conformality: illustration by a comparison of full beamlet IMRT, few-segment IMRT (fsIMRT) and conformal unmodulated radiotherapy," Phys Med Biol 48, 2051-2062 (2003).

[14] M. M. Coselmon, J. M. Moran, J. D. Radawski, B. A. Fraass, "Improving IMRT delivery efficiency using intensity limits during inverse planning," Med Phys 32, 1234-1245 (2005).

[15] S. B. Crowe, T. Kairn, N. Middlebrook, B. Sutherland, B. Hill, J. Kenny, C. M. Langton, J. V. Trapp, "Examination of the properties of IMRT and VMAT beams and evaluation against pre-treatment quality assurance results," Phys Med Biol 60, 2587-2601 (2015).

[16] W. Du, S. H. Cho, X. Zhang, K. E. Hoffman, R. J. Kudchadker, "Quantification of beam complexity in intensity-modulated radiation therapy treatment plans," Med Phys 41, 021716 (2014).

[17] A. L. McNiven, M. B. Sharpe, T. G. Purdie, "A new metric for assessing IMRT modulation complexity and plan deliverability," Med Phys 37, 505-515 (2010).

[18] K. C. Younge, M. M. Matuszak, J. M. Moran, D. L. McShan, B. A. Fraass, D. A. Roberts, "Penalization of aperture complexity in inversely planned volumetric modulated arc therapy," Med Phys 39, 7160-7170 (2012).

[19] C. K. McGarry, C. D. Chinneck, M. M. O'Toole, J. M. O'Sullivan, K. M. Prise, A. R. Hounsell, "Assessing software upgrades, plan properties and patient geometry using intensity modulated radiation therapy (IMRT) complexity metrics," Med Phys 38, 2027-2034 (2011).

[20] S. B. Crowe, T. Kairn, J. Kenny, R. T. Knight, B. Hill, C. M. Langton, J. V. Trapp, "Treatment plan complexity metrics for predicting IMRT pre-treatment quality assurance results," Australas Phys Eng Sci Med 37, 475-482 (2014).

[21] T. Bortfeld, J. Burkelbach, R. Boesecke, W. Schlegel, "Methods of image reconstruction from projections applied to conformation radiotherapy," Phys Med Biol 35, 1423-1434 (1990).

[22] J. Llacer, T. D. Solberg, C. Promberger, "Comparative behaviour of the dynamically penalized likelihood algorithm in inverse radiation therapy planning," Phys Med Biol 46, 2637-2663 (2001).

[23] S. V. Spirou, C. S. Chui, "A gradient inverse planning algorithm with dose-volume constraints," Med Phys 25, 321-333 (1998).

[24] R. Tibshirani. T. Hastie, Jerome Friedman, *The Elements of Statistical Learning: Data Mining, Inference, and Prediction*, Second ed. (Springer, 2009).

[25] T. Hastie, R. Tibshirani. Jerome Friedman, "Regularization Paths for Generalized Linear Models via Coordinate Descent" J Stat Softw 33, 1-22 (2008).

[26] J. B. Robert Tibshirani, J. Friedman, T. Hastie, N. Simon, J. Taylor, R. J. Tibshirani, "Strong Rules for Discarding Predictors in Lasso-type Problems" Journal of the Royal Statistical Society: Series B (Statistical Methodology) 74, 245-266 (2010).

[27] T. Harris, J. M. Hilbe, J. W. Hardin, "Modeling count data with generalized distributions," Stata J 14, 562-579 (2014).

[28] A. Molineu, N. Hernandez, T. Nguyen, G. Ibbott, D. Followill, "Credentialing results from IMRT irradiations of an anthropomorphic head and neck phantom," Med Phys 40, 022101 (2013).

What is claimed is:

1. A method comprising:
receiving one or more plan parameters of a first radiation treatment plan for a first patient and one or more passing rate data for the first radiation treatment plan;
generating a predictive model for passing rate data from the plan parameters of the first radiation treatment plan and the one or more passing rate data for the first radiation treatment plan;
receiving one or more plan parameters of a second radiation treatment plan for a second patient; and
applying the predictive model to the plan parameters of the second radiation treatment plan to generate one or more predicted passing rate data for the plan parameters for the second radiation treatment plan for the second patient.

2. The method according to claim 1, further comprising extracting one or more features associated with failure modes from the one or more passing rate data for the first radiation treatment plan.

3. The method according to claim 1, wherein the plan parameters of a first radiation treatment plan comprise organ volume data for the first patient and wherein the plan parameters of a second radiation treatment plan comprise organ volume data for the second patient.

4. The method according to claim 1, wherein the plan parameters of a first radiation treatment plan comprise one or more of the following parameters: radiation energies utilized in a treatment plan; parameters characterizing collimator jaw positions used in a treatment plan; parameters characterizing collimator angles used in a treatment plan; parameters describing a distribution of multi-leaf collimator (MLC) leaf pair openings used for delivery of a treatment plan; parameters describing an area of MLC and jaw defined apertures in delivery control points for a treatment plan; parameters relating monitor units utilized in plan to fractional plan dose; parameters describing MLC aperture geometry in each delivery control point; parameters describing a proportion of radiation delivered at different distances from a central axis; parameters describing a proportion of radiation delivered with different MLC leaf geometries; parameters describing MLC and jaw geometries; parameters describing Linac limitations; parameters describing limitations of a dose calculation algorithm; and parameters describing a calculated dose pattern of a treatment plan projected on a phantom.

5. The method according to claim 1, wherein the plan parameters of a first radiation treatment plan are weighted by the proportion of total monitor units delivered in each control point to the total monitor units delivered in the radiation treatment plan.

6. The method according to claim 3, wherein the organ volume data comprise one or more of the following parameters: Gross Tumor Volume to critical organs, organ type, and dose constraints.

7. The method according to claim 1, wherein the passing rate data for the first treatment plan comprises dose difference data, distance to agreement data, gamma passing rate data, or a combination thereof.

8. The method according to claim 1, wherein the predictive model is a generalized linear model.

9. The method according to claim 1, wherein the predictive model is generated using a Lasso selection method.

10. The method according to claim 2, wherein a failure mode is defined as having greater than 3 percent dose difference and/or 3 mm distance to agreement.

11. The method according to claim 2, wherein a failure mode is defined as having greater than 2 percent dose difference and/or 2 mm distance to agreement.

12. The method according to claim 1, further comprising modifying the second treatment plan if the generated pass rates comprise a failure mode.

13. The method according to claim 1, further comprising treating the patient in accordance with the second treatment plan if the generated pass rates do not comprise a failure mode.

14. A system for generating predictive passing rates for radiation therapy comprising:
a data-processing system;
a plan database comprising one or more radiation treatment plans for a first patient;
a passing rate database comprising one or more passing rates associated with each of the radiation treatment plans in the plan database; and
a predictive model for generating predictive passing rates based on the plan database and the passing rate database;
wherein the data-processing system receives the one or more radiation treatment plans from the plan database and the one or more passing rates from the passing rate database and applies the predictive model to organ data for a second patient and to one or more radiation treatment plan parameters for the second patient to generate one or more predicted passing rates for the one or more radiation treatment plan parameters for the second patient.

15. The system according to claim 14, wherein the predictive model is a generalized linear model.

16. The system according to claim 14, wherein the predictive model is generated using a Lasso selection method.

17. The system according to claim 14, wherein the predictive model is a machine learning model.

* * * * *